(12) United States Patent
Gordon et al.

(10) Patent No.: US 9,402,760 B2
(45) Date of Patent: Aug. 2, 2016

(54) IN SITU MOLDED ORTHOTIC AND METHOD FOR ITS FABRICATION

(76) Inventors: Christopher Burnside Gordon, Cincinnati, OH (US); Pilar Reyna Gordon, Cincinnati, OH (US)

(*) Notice: Subject to any disclaimer, the term of this patent is extended or adjusted under 35 U.S.C. 154(b) by 502 days.

(21) Appl. No.: 13/521,285

(22) PCT Filed: Aug. 18, 2011

(86) PCT No.: PCT/US2011/048276
§ 371 (c)(1),
(2), (4) Date: Jul. 10, 2012

(87) PCT Pub. No.: WO2012/024506
PCT Pub. Date: Feb. 23, 2012

(65) Prior Publication Data
US 2012/0296249 A1 Nov. 22, 2012

Related U.S. Application Data

(60) Provisional application No. 61/374,823, filed on Aug. 18, 2010.

(51) Int. Cl.
*A61F 5/00* (2006.01)
*A61F 5/37* (2006.01)
*A61F 5/058* (2006.01)

(52) U.S. Cl.
CPC ........... *A61F 5/3707* (2013.01); *A61F 5/05891* (2013.01)

(58) Field of Classification Search
CPC ............ A42B 3/00; A42B 3/12; A42B 3/122; A42B 3/20; A42B 3/08; A42B 3/16; A42B 3/18; A42B 3/125; A42B 3/124; A42B 3/062; A42B 3/121; A42B 3/127; A42B 3/324; A42B 3/0473; A01G 31/00; F16C 27/066; A41D 13/05; A41D 13/0512; A41D 13/0531; A41D 13/0593; A41D 31/005; A41D 13/0155; A41D 13/0506; A41D 13/0562; A41D 13/0581; A41D 13/065; A41D 2600/102; A63B 71/10; A63B 71/1291; A63B 2208/01; A63B 2208/12; A61F 5/01; A61F 5/3707
USPC .......................... 602/17–18; 2/414, 417, 425; 128/857–858
See application file for complete search history.

(56) References Cited

U.S. PATENT DOCUMENTS 3,563,234 A 2/1971 Umstead
3,653,234 A 4/1972 Gillespie
(Continued)

FOREIGN PATENT DOCUMENTS

AT 322230 7/1971
DE 22 50 681 4/1974

OTHER PUBLICATIONS

International Prelminary Report on Patentability and Written Opinion of the International Searching Authority for PCT/US11/48276 dated Sep. 26, 2013.
(Continued)

*Primary Examiner* — Michael Brown
(74) *Attorney, Agent, or Firm* — Tucker Ellis, LLP

(57) ABSTRACT

An orthotic helmet and methods for fabrication and use thereof. The orthotic is molded in situ on a growing infant's head for the treatment of plagiocephaly, postsurgical cranial molding, or other desired treatment plans. The helmet makes contact in areas where cranial shape and volume are adequate, and no contact in areas of planned cranial growth. The helmet includes a shell, a bladder system which can be filled with a viscoelastic expandable foam, a fastener and a retaining strap. In the areas of deficient cranial volume, a volume of modeling putty equivalent to the target growth volume is placed against the cranium, manually molded until the planned target volume and form have been attained, and the helmet is molded in place over this spacer material. The spacer is then removed, and the helmet is then worn continuously until resolution of the deformity or attainment of planned form is reached.

42 Claims, 9 Drawing Sheets

(56) References Cited

U.S. PATENT DOCUMENTS

| | | | |
|---|---|---|---|
| 3,726,620 A | 4/1973 | Morton | |
| 3,882,546 A | 5/1975 | Morton | |
| 3,994,020 A * | 11/1976 | Villari | 2/413 |
| 3,994,022 A * | 11/1976 | Villari et al. | 2/413 |
| 4,020,507 A | 5/1977 | Morton | |
| 4,060,855 A * | 12/1977 | Rappleyea | 2/413 |
| 4,114,197 A | 9/1978 | Morton | |
| 4,309,990 A | 1/1982 | Brooks et al. | |
| 4,345,338 A | 8/1982 | Frieder, Jr. et al. | |
| 4,450,833 A | 5/1984 | Brooks et al. | |
| 4,683,877 A | 8/1987 | Ersfeld et al. | |
| 4,776,324 A | 10/1988 | Clarren | |
| 4,828,325 A | 5/1989 | Brooks | |
| 4,888,225 A | 12/1989 | Sandvig et al. | |
| 4,903,690 A | 2/1990 | Campbell | |
| 4,946,726 A | 8/1990 | Sandvig et al. | |
| 5,002,047 A | 3/1991 | Sandvig et al. | |
| 5,038,312 A | 8/1991 | Kojima | |
| 5,056,162 A | 10/1991 | Tirums | |
| 5,094,229 A | 3/1992 | Pomatto et al. | |
| 5,195,945 A | 3/1993 | Sandvig et al. | |
| 5,308,312 A | 5/1994 | Pomatto et al. | |
| 5,324,460 A | 6/1994 | Briggs | |
| 5,449,478 A | 9/1995 | Gay et al. | |
| 5,581,832 A | 12/1996 | Bridley | |
| 5,699,902 A | 12/1997 | Sperry et al. | |
| 5,873,221 A | 2/1999 | Sperry et al. | |
| 5,891,372 A | 4/1999 | Besset et al. | |
| 5,899,325 A | 5/1999 | Bertram et al. | |
| 5,915,503 A | 6/1999 | Enright | |
| 5,951,503 A | 9/1999 | Pomatto | |
| 5,996,782 A | 12/1999 | Sperry et al. | |
| 6,006,381 A | 12/1999 | Tandrup | |
| RE36,583 E | 2/2000 | Pomatto et al. | |
| 6,052,849 A | 4/2000 | Dixon et al. | |
| 6,178,560 B1 | 1/2001 | Halstead et al. | |
| 6,226,817 B1 | 5/2001 | Rubio | |
| 6,260,553 B1 | 7/2001 | Mann | |
| 6,266,832 B1 | 7/2001 | Ezell | |
| D448,227 S | 9/2001 | Straub | |
| 6,298,497 B1 * | 10/2001 | Chartrand | 2/414 |
| 6,346,353 B1 | 2/2002 | Wang et al. | |
| 6,351,853 B1 | 3/2002 | Halstead et al. | |
| 6,421,855 B2 | 7/2002 | Mann | |
| 6,423,019 B1 | 7/2002 | Papay et al. | |
| 6,428,484 B1 | 8/2002 | Battmer et al. | |
| 6,428,494 B1 | 8/2002 | Schwenn et al. | |
| 6,460,207 B1 | 10/2002 | Papay et al. | |
| 6,473,923 B1 | 11/2002 | Straub | |
| 6,490,730 B1 | 12/2002 | Lyden | |
| 6,564,408 B2 | 5/2003 | Van Vuuren | |
| 6,572,572 B2 | 6/2003 | Pomatto et al. | |
| 6,591,428 B2 | 7/2003 | Halstead et al. | |
| 6,592,536 B1 | 7/2003 | Argenta | |
| 6,695,801 B1 | 2/2004 | Toronto et al. | |
| 6,829,794 B2 | 12/2004 | Lenyo | |
| 6,939,316 B2 | 9/2005 | Sklar et al. | |
| 6,983,839 B2 | 1/2006 | Bertram et al. | |
| 7,070,238 B1 | 7/2006 | Alexander et al. | |
| 7,153,284 B2 | 12/2006 | Argenta | |
| 7,177,461 B2 | 2/2007 | Littlefield et al. | |
| 7,242,798 B2 | 7/2007 | Littlefield et al. | |
| 7,542,950 B2 | 6/2009 | Littlefield et al. | |
| 7,563,237 B1 | 7/2009 | Murphy | |
| 7,566,313 B1 | 7/2009 | Argenta | |
| 7,901,370 B1 | 3/2011 | Van Griffin et al. | |
| 8,827,939 B2 | 9/2014 | Slatten | |
| 9,182,208 B2 | 11/2015 | Ebisawa | |
| 2001/0042269 A1 | 11/2001 | Mann | |
| 2002/0042954 A1 | 4/2002 | Straub | |
| 2002/0174488 A1 | 11/2002 | Appleton | |
| 2003/0033674 A1 | 2/2003 | Mann | |
| 2003/0145384 A1 | 8/2003 | Stelnicki | |
| 2003/0195450 A1 | 10/2003 | Argenta | |
| 2004/0015118 A1 | 1/2004 | Sklar et al. | |
| 2005/0079252 A1 | 4/2005 | Kendig et al. | |
| 2006/0101559 A1 | 5/2006 | Moore, III et al. | |
| 2009/0078595 A1 | 3/2009 | McKinley | |
| 2010/0178414 A1 | 7/2010 | Judge | |
| 2011/0039049 A1 * | 2/2011 | Chow | 428/71 |
| 2011/0203038 A1 | 8/2011 | Jones, Jr. | |
| 2011/0273286 A1 | 11/2011 | Sklay | |
| 2015/0352813 A1 | 12/2015 | Galloway et al. | |

OTHER PUBLICATIONS

Pediatrics vol. 103 No. 3 Mar. 1999 "Multiple-birth Infants at Higher Risk for Development of Deformational Plagiocephaly" Timothy R. Littlefield, MS, et al.

Pediatrics vol. 109 No. 1 Jan. 2002 "Multiple-birth Infants at Higher Risk for Development of Deformational Plagiocephaly: II. Is one Twin at Greater Risk?" Timothy R. Littlefield, MS, et al.

Seminars in Pediatric (Neurology) "On the Current Incidence of Deformational Plagiocephaly: An Estimation Based on Prospective Registration at a Single Center" Timothy R. Littlefield, MS, et al.

Cranial Molding Helmet Information and Wearing Instructions (Internet); Copyright 2007 Orthotic Solutions.

Star-Cranial Remolding Orthoses (Brochure) 2007, www.orthomerica.com.

Frontiers in Bioscience 14,4962-4967,m Jun. 1, 2009 Burns as a model of SIRS—Punam Dahiya.

The American Journal of Pathology, Nov. 1947, vol. XXIII, No. 6 Studies of Thermal Injury III. The Pathology and Pathogenesis of Cutaneous Burns; An Experimental Study Moritz.

What is DOC Band? Web page; Copyright 1997-2011 Cranial Technologies Inc.

KidCap FAQs—For Physicians on our Plagiocephaly Therapy and Treatment—Web page; Copyright 2006-2009, Eastern Cranial Affiliates, LLC.

Ballert Orthopedic of Chicago—"Cranial Molding Helmet Instruction Sheet".

Technical Strategies—An Assistive Device for the Treatment of Positional Plagiocephaly Benjamin S. Carson, MD, Daniel Munoz, Gayle Gross, OTR, Craig A Vanderkolk,MD, Carol S. James, PA-C, Judy Gates, PA, Marisa North, Michael McKnight, Michael Guarnieri, PHD.

http://www.gillettechildrens.org/default.cfm?PID=1,17.4.15.7.1 Gillette Children's speciality Healthcare CranioCap FAQs.

http://www.crainaltech.com/index.php?option=com_content &view=art "What is the DOC Band?" 1997-2011 Cranial Technologies, Inc.

A Pneumatic Orthotic Cranial Molding Helmet for Correcting Positional Plagiocephaly Walter T. Lee, MD, Kirsten Richard, CP, James Redhed, CPO, Frank A. Papay, MD Copyright Mutaz B. Habal, M.D.

Pediatrics vol. 99 No. 2 Feb. 1997 Diagnosis and Management of Posterior Plagiocephaly Ian F. Pollack, MD, H. Wolfgang Losken, MBCHB, FCS(SA), Patricia Fasick, OTR/LS.

510(k) Summary—K003035—Clarren Helmet, Aug. 2000 Children's Hospital & Regional Medical Center.

510(k) Summary—K003630-DANMAR Products, Inc.—Karen A. Lindner—Danmar Products Cranial Helmet Nov. 22, 2000.

510(k) Summary—K010273, p. 113—Summary of Effectiveness and Safety—Apr. 25, 2001—Orthotic Solutions, LLC, Fairfax, VA, Joseph F. Terpenning, CO—Per Federal Food, Drug, and Cosmetic Act 513(I)(3)(A).

510(k) Summary—K012804—Aug. 14, 2001, Scott E. Allen, C.P. Tradename: Plagiocephalic Applied Pressure Orthosis P.A.P. Orthosis.

510(k) Summary K012830, p. 1-3, Lerman & Son, Aug. 20, 2001 Tradename: Lerman & Son Cranial Orthosis Helmet (Cranial Helmet).

510(k) Summary K012920, p. 1-3, Carol Hentges, Fairview Orthopedic Laboratory, Fairview Rehabilitation Services, Orthotics and Prosthetics, Minneapolis, MN—Tradename: Molded Cranial Helmet (Cranial Orthosis-21C.F.R. Section 882.5970) Nov. 28, 2001.

510(k) Summary—K013458—Children's Hospital, Omaha, NE (Cranial Orthosis), Oct. 17, 2001.

(56) References Cited

OTHER PUBLICATIONS

510(k) Summary—K013700—Precision Prosthetics and Orthotics, Inc., Nov. 7, 2001-Tradename: Cranial Orthosis.
510(k) Summary—K013719—Dr. James H. Campbell, Becker Orthopedic, Troy, MI Feb. 5, 2002 (Cranial Orthosis).
510(k) Summary—K014012—Jan. 28, 2002—Summary of Safety and Effectiveness, Doc Brand, Registration No. KI27902, Cranial Technologies, Inc.
510 (k) Summary—K020448—Apr. 12, 2002, Eastern Cranial Affiliates, Whitestone, NY—Static Cranioplasty Orthosis (Cranial Orthosis).
510(k) Summary—K021221 p. 1-3, Jul. 1, 2002, Orthotic & Prosthetic Lab, Inc., Thomas L. Malone-Cranial Molding Helmet, Class II, Cranial Orthosis, Code MVA, CFR 882.5970—Tradename: Cranial Orthosis.
510(k) Summary—K021918—Clarren Helmet (Orthomerica) and the STARScanner, Orthomerica Products, Inc., Orlando, FL, Deanna Fish, MS, CPO.
510(k) Summary—K022273—Cranial Symmetry System, Sep. 9, 2002, Beverly Hills Prosthetics Orthotics, Inc.
510(K) Summary—K023572—Michael J. Davidson, MPH,CPO, Rehabilitation Institute, Loma Linda University Medical Center, Jan. 13, 2003—Tradename: LLUMC Cranial Remolding Helmet (Clarren Helmet).
510(k) Summary K014215—Sep. 9, 2004, Otto Bock HelthCare LP, Minneapolis, MN, Registration No. 2182293, Cranial Helmet, Class: II.
510(k) Summary K042385, Dec. 17, 2004, Cranial Technologies, Inc., Timothy R. Littlefield—Doc Band-PostOp.
510(k) Summary—K063098,Feb. 16, 2006, Boston Brace International, Inc., James Wynne, CPO, Director of Education, Boston Band Cranial remolding Orthosis (Cranial Orthosis).
510(k) Summary—K063133, Jul. 12, 2007, p. 1-4, Cranial Solutions, Pompton Lakes, NJ, Tradename: Cranial Solutions Orthosis (CSO).
510(k) Summary—K063395, Dec. 22, 2006—Orthotic & Prosthetic Lab, Inc., Webster Groves, MO, Thomas L. Malone, Cranial Molding Helmet—Tradename: O&P Bivalve Cranial Molding Helmet.
510(k) Summary—K070694—Sep. 10, 2007—Mike Miner, Kaysville, UT—Craniocephalic Custom Remolding Drthtosis.
510(k) Summary—K081787—BioSculptor Corporation, Hialeah, FL-CAMLab Cranial Orthosis Helmet.
510(k) Summary—K090587—Orthomerica Products, Inc., Newport Beach, CA—Registration No. 1058152, Jun. 9, 2009—STARlight.
510(k) Summary K090341 Kay Fuller, RAC—Cranial Reshaping Orthosis (Oct. 13, 2009).
Pediatrics—Prevention and Management of Positional Skull Deformities in Infants, John Persing, Hector James, Jack Swanson, John Kattwinkel, Committee on Practice and Ambulatory Medicine, Section on Plastic Surgery and Section on Neurological Surgery—2003; 112,199 http://pediatrics.aappublications.org/content/112/1/199.full.html.
Setting Temperatures of Synthetic Casts, M.H. Pope, Phd, G. Callahan, R. Lavalette, RN, ONP, Burlington, VT copyright 1985 by The Journal of Bone and Joint Surgery, Incorporated.
Press Release: Plagiocephaly Research by Suzanne Browne, Trinity College Dublin.
Clinical Report: Acquiring Craniofacial Symmetry and Proportion though Repositioning, Therapy, and Cranial Remolding Orthoses by Dulcey Lima, CO, OTR/L and Deanna Fish, MS, CPO.
Cranial Growth Unrestricted During DOC Treatment of Plagiocephaly-T. Littlefield, K. Kelly, J. Pomatto, K. Manwaring, S. Beals, E. Joganic.
Custom Molded Seating by Cindi Petito, OTR/L, ATP, CAPS, Mary Hitt Young, ATP, RRTS—Rehab Management, Mar. 2011.
Deformational Brachycephaly in Supine-Sleeping Infants—John M. Graham, Jr., MD,SCD, Jeannie Kreutzman, CPNP, MSN, Dawn Earl, CPNP, MSN Andy Halberg, BS, Carlos Samayoa, MPH, Xiuqing Guo, Phd The Journal of Pediatrics, Feb. 2005.
Thermal Injury with Contemporary Cast-Application Techniques and Methods to Circumvent Morbidity; Halanski, et al. The Journal of Bone and Joint Surgery 2007; 89:2369-2377.
Dynamic Orthotic Cranioplasty Brochure—Balance, Symmetry—Reshaping Children's Lives.
Journal of Orthopaedic Surgery and Research—Factors Contributing to the temperature beneath plaster or fiberglass aast material, Michael J. Hutchinson and Mark R. Hutchinson, Published Feb. 25, 2008.
Joint Industry Foam Standards and Guidelines, Section 1.0, Published Jul. 1994.
Management of Deformational Plagiocephaly: Repositioning Versus Orthotic Therapy—John M. Graham, Jr., MD, SCD, et al. (The Journal of Pediatrics—Feb. 2005).
Importance of Early Recognition and Treatment of Deformational Plagiocephaly with Orthotic Cranioplasty Kevin M. Kelly, Ph.d, et al. Cleft Palate-Craniofacial Journal, Mar. 1999, vol. 36 No. 2.
American Academy of Pediatrics—Jul. 31, 2001 "Incidence of Cranial Asymmetry in Healthy Newborns", Wiebke K. Peitsch, Constance H. Keefer, Richard A. Labrie and John B. Mulliken.
UPO Journal of Prosthetics and Orthotics, vol. 15 No. 3, 2003—"Car Seats, Infant Carriers, and Swings: Their Role in Deformational Plagiocephaly", Timothy R. Littlefield, MS, Kevin M. Kelly, Phd, Jacque L. Reiff, RN,BS, Jeanne K. Pomatto, BOC.
510(k) Summary—K060986 Steven H. Warnock, M.D., P.C. Infant Sleep Positioner FRP, CFR 880.5680—Jul. 11, 2006.
J. Physiol. (1954) 126, 191-205 "Relationship Between Cutaneous Thermal Thresholds, Skin Temperature and Cross-Sectional Area of the Stimulus" by P.P. Lele. From the Department of Human Anatomy, University of Oxford Received Feb. 22, 1954).
FAQs—For Physicians on our Plagiocephaly Therapy and Treatment—infinitetech.org, 2006-2009.
Official Journal of the American Academy of Pediatrics "Long,-Term Developmental Outcomes in Patients with Deformational Plagiocephaly", Robert I. Millier, et al., Pediatrics 2000; 105; e26, DOI:10.1542/peds.105.2e26 http://pediatrics.aappublications.org/content/105/2/e26.full.html.

* cited by examiner

IN SITU MOLDED ORTHOTIC AND METHOD FOR ITS FABRICATION

CROSS-REFERENCE TO RELATED APPLICATIONS

This application claims priority to the International Application No. PCT/US11/48276, having the international filing date of Aug. 18, 2011, which is based on and claims priority to U.S. provisional patent application Ser. No. 61/374,823 filed Aug. 18, 2010, the disclosure of which is included herein by reference in its entirety.

BACKGROUND

1. Technical Field

The embodiments described herein relate to an orthotic system molded in situ on the head of an associated patient, to the fabrication or set up methods of the orthotic system on the patient's head, and to the use of a cranial orthotic system for the modification of cranial shape for treatment of, for example, plagiocephaly, post-operative cranial molding, and the like.

2. Background Art

Plagiocephaly is characterized by an abnormal cranial shape which can occur in response to external pressure, or due to premature fusion of cranial sutures in infancy. Infants who develop plagiocephaly can have additional distortion of other craniofacial structures in response to external molding pressure, frequently involving the orbit, face, and cranial base. This pressure can take the form of intrauterine contact with the maternal pelvis, prolonged pressure in the birth canal, or chronic pressure from sleeping in one position. Additional risk factors for developing positional or deformational plagiocephaly include multiple births, congenital torticollis or neck tightness, developmental delay or neurologic impairment which precludes normal infant movement, uterine abnormalities, and genetic influences.

The incidence of positional plagiocephaly has been rising due to increased numbers of infants sleeping in the supine position. In 1992, the American Academy of Pediatrics began the "Back to Sleep" campaign, maintaining that all infants should sleep in the supine position to decrease the incidence of crib death or SIDS (Sudden Infant Death Syndrome) which has been linked to prone or side sleeping. This has resulted in an epidemic of plagiocephaly which affects up to 1 in 8 live births in the U.S., according to some estimates. Despite the increased incidence of plagiocephaly, the campaign has resulted in a decrease in SIDS by more than 40%, and will likely continue into the foreseeable future. Therefore, measures to avoid plagiocephaly or treat it after it has developed have been devised.

Additionally, premature fusion of one or more of the cranial sutures can lead to similar alterations in cranial shape, called craniosynostosis. Conventional surgical therapy involves removing the cranial bones, physically remodeling them, and rigidly fixing them in place in their new form with plates, screws, or other mechanical fastening methods. A newer approach has evolved to permit endoscopic or minimally invasive release of the fused or synostotic cranial sutures. This method relies upon subsequent expansion of the growing brain to remodel the cranium, or the use of springs or appliances which cause expansion of the cranial vault, creating a role the use of molding helmets or orthotics for directing postoperative cranial growth.

A number of methods have been described to alter cranial shape, with historical examples dating back to the early early Olmec culture (1400 BC-400 AD) in what is today modern Mexico. These Mesoamerican inhabitants used external compression to alter cranial form for aesthetic purposes. In the modern era, external compression techniques have been used to treat plagiocephaly. The growing brain provides the impetus for early cranial growth, leading to expansion of the cranial vault across the cranial sutures, which are essentially biological expansion joints. Similarly, these forces are harnessed to permit remodeling or molding of the cranium.

There are several categories of devices or techniques known in the art which have been used for the treatment of plagiocephaly. These include simple positioning of the infant to minimize deforming forces, the use of wedges, pillows, or mattresses, and primitive helmet or band type orthoses.

Current recommendations for initial treatment for early positional plagiocephaly include positioning the infant so that there is no pressure on the flattened area of the cranium, relying upon periodic checks during the night to ensure compliance. This method is hampered by poor parental acceptance due to the need for frequently awakening during the night to check on the infant. Further, the infants often prefer to lie upon the flattened area, exacerbating the problem.

Other techniques to improve plagiocephaly can include the use of wedges or pillows to alter pressure on the infant's head. The success of these positioners is also hampered by the infant's activity level. Once they are capable of rolling over, they can move out of the desired sleep position.

Other strategies for redirecting pressure on the head include devices which tip or bolster the sleeping surface. These devices are also limited in utility by the mobility of the infant, who can move out of ideal position, thus rendering the mattress or pad device ineffective. Further, the force of gravity can only be transmitted to the cranium by the dependent portion of the head, limiting the overall distribution of the remodeling forces.

Another category of devices to treat plagiocephaly include orthotics and helmets that fall generally into the categories of active or passive cranial molding devices. The force of the growing brain can be directed to specific areas of the cranium by constraining growth in a portion of the head, permitting the growing brain to exert expansile forces in areas not covered by the orthotic. The first class of devices are designed to actively apply pressure to some or most of the cranial surface. Although these devices are marginally effective in modifying head shape, there are additional concerns that active molding appliances can result in more frequent soft tissue injury, hair loss, and potential discomfort to the patient, rendering this approach less desirable to the practitioner. Further, there are theoretical concerns that these devices can increase intracranial pressure, resulting in potential local injury to the brain, and potential developmental delay. The other class of cranial molding devices are roughly adapted to approximate the shape of the patient's head and, accordingly, do not actively exert pressure. There are some data which suggest these devices designed to function passively have less risk of elevating intracranial pressure, with less potential for affecting brain development. Passive cranial molding orthoses involve helmet or band-type devices which constrain head growth in areas of more normal shape, permitting further growth in areas in which the helmet either has less pressure, or does not make contact. These devices rely upon an intimate contact with portions of the more normally shaped cranium, constraining growth in these areas, and directing the expansile forces of the brain to the areas of the orthosis in which there is no contact with the cranium. These methods are most effective in modifying craniofacial shape during early infancy when craniofacial growth is rapid.

Within the category of helmet orthoses, methods of active cranial molding utilize pneumatic bladders to mold the head. However, these devices rely an initial plaster model of the infant's skull fabricated, followed by construction of a custom helmet with a plurality of pneumatic bladders to apply pressure to various parts of the head, thereby increasing molding forces and directing growth towards the portion of the helmet where there is no contact. This method has the drawback of imprecise direction of molding forces due to the limited number of bladders which can be included, difficulty in ensuring even application of pressure along the bladder margins, and the general drawback of the use of active molding forces, which may cause unforeseen problems to the growing brain.

Practitioners skilled in the art have recognized that customized cranial orthoses which are specially designed for each individual patient are most effective in restoring normal cranial form to the affected infant. These helmets have been historically fabricated by taking a plaster cast of the patient's head, using the plaster cast as a negative mold to create a positive mannequin form which is a fair representation of a copy of the patient's head shape, then molding a custom orthotic upon this mannequin head. Alternately, this process can be carried out with laser scanning to create a virtual model of the patient's head, followed by the creation of a stereolithographic or CAD milled model or mannequin of the patient's head, followed by custom molding of the orthotic device on the mannequin. These methods are somewhat effective, but are cumbersome, time-consuming, and expensive. Additionally, they require significant expertise in both computer image manipulation, and in fabrication of orthotic devices in order to achieve an acceptable result.

In practice, the use of a positive model upon which to create the molding helmet/orthosis, and the use of an expert system software utilizing an anthropomorphic database to generate a positive model of the desired head shape, requires a skilled orthotist to create the appropriate computer file modifications to design the appliance, the use of stereolithographic or CAD milling methods for creation of the intermediate mannequin, and multiple visits for the patients due to time constraints involved in the manufacturing process. Importantly to the patient's treatment regime, the creation of a positive model from either a physical cast or a virtual three-dimensional image requires at least two patient visits, including a first visit to acquire the actual or virtual mold of the patient's head, an interval to permit time to create the model and fabricate the orthotic upon the mannequin head, followed by a secondary visit to check the fit and form on the head of the patient. This typically takes weeks to carry out, resulting in significant expense and inconvenience to the patient's family and results in delay of treatment. More importantly, this indirect casting method creates inaccuracies in helmet fit related to the loss of detail which begins with the initial casting or laser scan, then in the generational conversion of scan data to CAD data, subsequent manipulation of those data, the creation of the negative molds, and finally with the secondary molding upon the mannequin head.

Most devices of this class use a layer of foam as the substrate to transfer pressure to the patient's head. In the majority of these devices, a solid sheet of the foam is heated and molded upon the positive form, followed by vacuum thermoforming of the polymer shell material upon the foam liner. This method uses manufacturing techniques which are unsuitable to application in situ on the patient's head owing in part to the specialized equipment and to the high temperatures needed for material forming and handling.

BRIEF SUMMARY

The embodiments described relate to an orthotic molded in situ on a body part of a patient such as an arm, leg, or preferably the head. The example embodiment includes a cranial orthotic molded in situ on the head of a target associated patient but the application is not limited to devices for the head and includes devices configured for use on and in situ molding to other body parts. In situ molding provides several advantages over prior art techniques of forming orthotic structures on proxies such as a mannequin form or the like. In accordance with an embodiment, a simple volumetric method is used for estimating a target molding volume, rather than the substantially more complicated and costly step as in the prior art of topographically determining the final contour on a mannequin. In the embodiment described herein, the determination of target volume is based on a simple estimation of differential volume of the two sides of the patient's head, followed by the use of a physical modeling putty as a temporary spacer material. The preferred modeling putty is hand-formable into any desired shape or shapes and is used in the embodiment directly upon the patient's head to create a temporary outer surface contour in the areas of desired cranial growth, permitting a rapid visual confirmation of symmetry with the more normal side. The modeling putty acts or functions like spacer material whereupon the remaining portions of the orthotic system are then placed and formed in situ upon the patient's head with the spacer putty material in place. A foamable or expandable material is selectively received into an expandable bladder of the orthotic system and permitted to harden or otherwise cure, creating a foam helmet liner in situ, over both the native cranium and the physical spacer material defining the target outer surface contour of the patient's head in the areas of desired growth. Use of the spacer material may not be needed for use of the subject orthotic on other body parts of the patient or user, however.

The embodiments described herein permit fabrication of a very accurately molded helmet in a single procedure or office visit saving time during critical cranial growth periods. In addition, molding of the orthotic directly upon the patient's head advantageously eliminates the need to physically create a positive model of the patient's head upon which to fabricate the orthosis, thus avoiding the cost and complexity of that portion of the process. Further, in situ molding results in a more even and accurate distribution of the pressure across the patient's head, avoiding pressure points and fit issues which affect indirectly fabricated orthoses of the prior art. Further, in situ molding of the subject orthotic system does not require trained orthotists to fabricate the device, but instead uses simple techniques accessible to an untrained practitioner. Yet still further, any fit issues or other problems that may arise with the orthotic during in situ molding or thereafter during use, can be easily visually recognized and remedied, wherein a new orthotic can be fabricated at the same visit.

In an embodiment, a two-part polyurethane foam is mixed then injected into the expandable bladder of the orthotic while on the patient's head and with the one or more putty material spacer members in place wherein the foam is permitted to harden in situ. A convenient form of the two-part polyurethane foam is used for storage and delivery of a flowable foam pad or liner. A laminated plastic bag coupled with a service port selectively operatively coupleable with a corresponding service port portion of the orthotic bladder is used in an embodiment for the delivery of the mixed foaming components to within the bladder of the orthotic for molding, still further simplifying the process. The bag has compartments holding the material components separated until use wherein walls between the compartments are selectively broken or otherwise removable to initiate the flowable and curing process.

In accordance with a method of an embodiment, the patient's head volume is estimated using mechanical methods such as volume displacement, "bed of nails" or 3d scanning or equivalent technology or any other form of volume estimation. In a further preferred embodiment, the patient's head is scanned using a 3-dimensional camera or scanner familiar to those skilled in the art. The data from this scan are converted into a three-dimensional representation of the craniofacial structures imaged by the scan. These are then imported into a suitable system such as a software system for example for segmentation.

In accordance with an embodiment, these data are segmented into two volumes by assigning a midline plane based upon anatomic landmarks known to the skilled practitioner. Similarly, the inferior limit of the volumes to be compared is defined. This could represent an arbitrary axial plane or the volume covered by the helmet orthotic. The two sides are then measured volumetrically, and the lesser volume is subtracted from the greater volume, yielding the estimated volume of planned expansion.

Then, in accordance with an embodiment, a volume of modeling putty is measured out to correspond to the volume of planned expansion. This modeling putty is then placed within a pocket in a modeling cap or garment having the general size, shape, and characteristics of a rubber bathing cap, to hold it in place on the patient's head. The putty is then manually molded to the desired contour of cranial expansion, in accordance with the methods, providing a direct means of preserving the final desired contour of the internal aspect of the orthosis wherein an inner surface of the putty conforms to the surface of the patient's head in the area of irregularity, and the outer surface of the putty spacer defines the desired final outer contour of the patient's head after cranial growth.

Still further in accordance with a further embodiment, the practitioner may selectively place a thicker layer in areas of more desired growth, and a thinner layer in more symmetric areas which require less growth. Additionally, the putty can be selectively placed discontinuously as necessary or desired, to permit multiple areas of cranial molding.

In an alternative embodiment, a practitioner skilled in the art selectively estimates the amount of putty required to produce a symmetric cranial form without using a scanner or equivalent imaging method, relying instead upon visual cues to guide the placement and volume of the modeling putty.

Still further, additional putty can be placed in areas where further growth is desired bilaterally, or on the larger of the two sides, in areas where desired prominences would be located, or where no pressure is desired, such as in areas of previous surgery.

Then, in accordance with the example embodiment, the helmet orthosis is placed upon the patient's head and fastened using a chin strap component or the like. The foam is then activated and introduced into the bladder of the helmet after mixing the components and catalyst, or activated within the bladder by rupturing the cells or ampoules containing the foam precursors. The activated foam fills the bladder as it expands until it has compressed the internal aspect of the bladder against both the patient's head and the surface of the putty. For other embodiments, the bladder expands against the patient's arm, leg, or other body part as desired to immobilize the portion of the body part. As the foam further expands, excess pressure is avoided by permitting the foam to flow out of effluent tubes provided in the bladder whereby the excess foam may flow into collection bags coupled with the bladder, or into an extra volume area provided in a self-contained bladder system of an embodiment. Pressure relief vents or holes are desirable in the bladder and are sized and located in accordance with the chemical formulation of the foam, for permitting excess gas or steam produced during the polymerization of the foam to be relieved as necessary or desired from the bladder while disposed in the gap between the patient's head and the orthosis. In one embodiment, the vents or holes are formed in the bladder using a "bed of nails" technique wherein a plurality of spaced apart pins or needles arranged on a form are movable relative to the bladder to simultaneously pierce the bladder at plural locations forming a corresponding set of plural vent holes therein.

The foam is then permitted to cure or harden while the orthosis is in place on the head of a patient. The orthosis is then removed to permit final curing. Degassing or aeration of the foam molding agent may be desired or required to avoid excessive hardening or localized hardening in accordance with the formulation of foam. Degassing or aeration could be accomplished in accordance with the embodiment by removing inlet and/or outlet tubes of the bladder if provided, removing some or all of the internal aspect of the bladder, or by altering the quantity or location of the vent holes.

After the curing of the molding agent, the helmet orthosis has an inherent internal contour which corresponds to the desired cranial form defined by portions of the patient's head and by the exterior surface of the model putty spacer members. The one or more pieces of modeling putty are removed and discarded having served their purpose during the molding of providing temporary spacer members between the patient's head and the bladder containing the moldable material. Removal of the temporary spacer members results in one or more gaps between the patient's head and the bladder containing the moldable material, wherein the gaps define one or more volumes into which the growth of the patient's skull may be directed. Thereafter, during a treatment embodiment, the helmet is worn nearly constantly by the patient, constraining cranial growth in areas of contact between the patient's head and the hardened bladder member, and permitting growth in areas relieved of contact by previous placement, then removal, of modeling putty until the objective of differential cranial molding is achieved.

It may be advantageous to trim the excess foam where contact is not necessary, such as in areas adjacent to the neck or vertex areas of the patient. Further modification of the helmet orthosis can be performed selectively at any time, if so desired, by grinding or relieving foam in areas of excess prominence such as at the top in the filler port area for example, or adding shims in areas of inadequate projection of the foam liner or both.

Accordingly, it is an overall object to permit the direct molding of a custom fitted orthotic in situ upon a body part of a patient by means of a self-expanding foam and bladder system contained during molding in an outer resilient shell having the general shape of the target body part.

Accordingly, it is a further overall object to permit the direct molding of a custom fitted cranial orthotic in situ upon the patient's head by means of a self-expanding foam and bladder system.

A further object is to utilize a self-contained foaming system to simplify delivery of the custom orthotic and limit the cost and complexity of said system.

A further object is to provide a more rapid delivery of the custom fabricated orthotic by eliminating steps involved in the indirect fabrication methods, thereby decreasing treatment time and improving patient outcome through earlier intervention.

An additional object is to use a volumetric method of estimation of cranial asymmetry to avoid the complexity of fabrication of a topographically corrected mannequin as the molding form.

A further object of the method is to avoid the limitations of indirect fabrication methods by utilizing modeling putty as a physical spacer to define zones of desired contact of the helmet during the molding process.

It is still a further object to make this technology accessible to a less skilled practitioner to permit delivery of the orthoses of the present invention by primary care providers without the need to refer patients to secondary providers for measurement and fabrication of the orthoses.

BRIEF DESCRIPTION OF THE DRAWINGS

The embodiments will be more easily understood by reading the detailed description of the invention along with the accompanying illustrations in which.

DETAILED DESCRIPTION OF THE EMBODIMENTS

Figure 1:
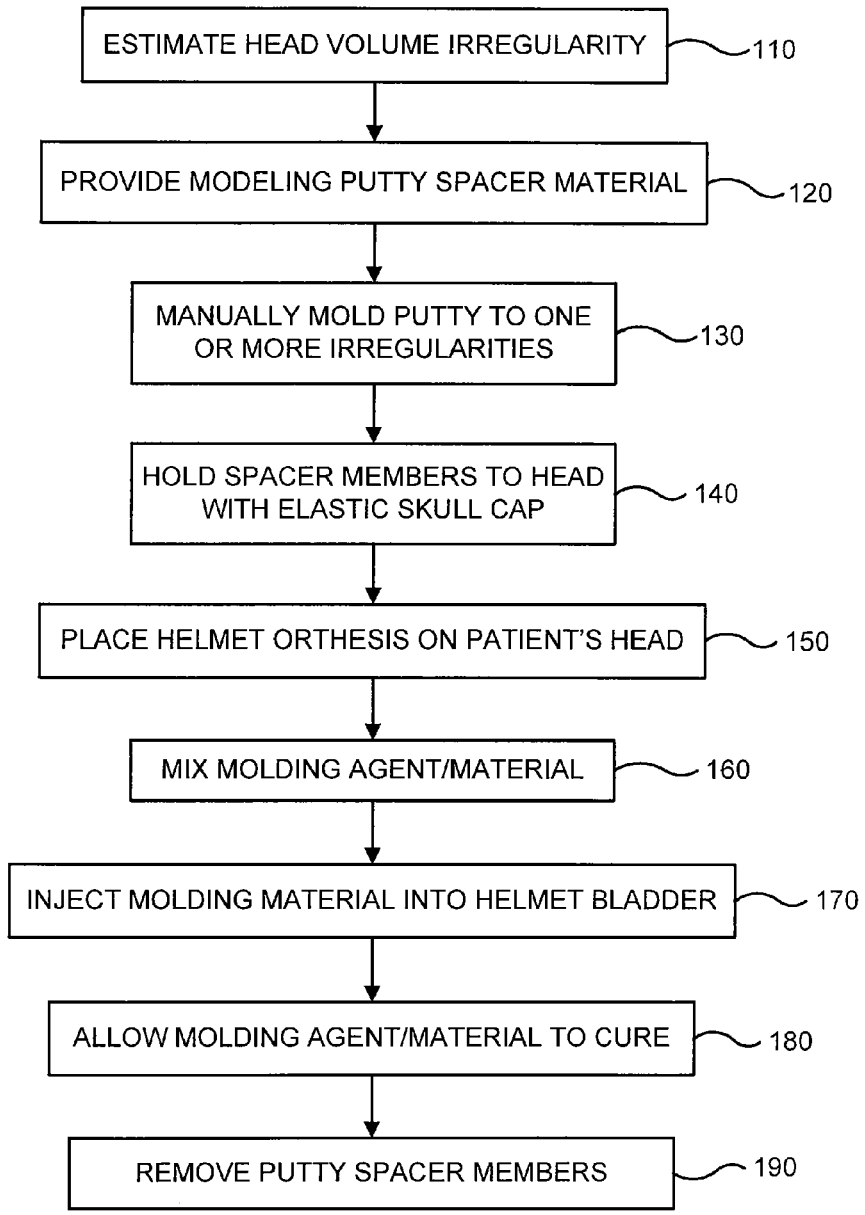
FIG. 1 illustrates a flow chart showing a method of fabricating a cranial orthotic in accordance with an example embodiment.

With reference now to the drawings where the showings are for purposes of illustrating the example embodiments only, and not for purposes of limiting same, the Figures show embodiments of a molded orthotic, methods of fabricating a molded orthotic, and methods of treatment using a molded orthotic. With reference first to FIG. 1 a method 100 of fabricating a molded orthotic in accordance with an embodiment is illustrated. In an initial step 110, a patient's head volume is estimated for use in determining and locating one or more head volume irregularities. The estimations may be performed visually, using mechanical methods such as volume displacement "bed of nails," by 3d scanning or equivalent technology, or by using any other form of volume estimation that may be convenient or desired. In a first preferred embodiment, selected steps of the method 100 are performed visually where applicable and, in another embodiment, the patient's head is scanned using a 3-dimensional camera or scanner familiar to those skilled in the art. The data from this scan are converted into a three-dimensional representation of the craniofacial structures imaged by the scan. These are then imported into a suitable system such as a software system for example for segmentation to be described in greater detail below.

In a further step 120 in accordance with an embodiment, a volume of modeling putty is measured out to correspond to the volume of planned expansion based on the acquired data and segmentation results. Although modeling putty is used as spacer material in a manner to be described below, it is to be appreciated that any form of malleable material having suitable shape retaining and hand-workable properties may be used equivalently. In an alternative embodiment, a practitioner skilled in the art could estimate the amount of putty required to produce a symmetric cranial form without using a scanner or equivalent imaging method, relying upon visual cues during live first person inspection of the patient's head to guide the placement and volume of the modeling putty. The putty is then manually molded in step 130 to the desired contour of cranial expansion, in accordance with the methods, providing a direct means of preserving the final desired contour of the internal aspect of the orthosis. This modeling putty is then placed in step 140 within a pocket in the modeling cap or garment to hold the putty portions as one or more temporary spacer members in place on the patient's head. Still further in accordance with an embodiment, the practitioner may selectively place a thicker layer in areas of more desired growth, and a thinner layer in more symmetric areas which require less growth. Additionally, the putty can be placed discontinuously, to permit multiple areas of molding. Still further in accordance with an example embodiment, additional putty can be placed in areas where further growth is desired bilaterally, or on the larger of the two sides, in areas where desired prominences would be located, or where no pressure is desired, such as in areas of previous surgery.

Then, with the one or more portions of putty spacer material held in place by the elastic skull cap, the helmet orthosis is placed in step 150 upon the patient's head and fastened thereon using a chin strap or the like to be described below. The foam molding material to be used with the helmet is mixed for activation in step 160 and is then introduced in step 170 into the bladder of the helmet. In one embodiment, the components and catalyst are mixed in a separate pouch. They may, however, be activated within the bladder by rupturing the cells or ampules containing the foam precursors or by any other suitable means, embodiments of which will be described in greater detail below. The compartments of the example pouch may be formed by elongate clamps located at selected positions holding the pouch therebetween wherein removal of the clamps permits communication of the molding agent components in adjacent compartments and wherein ordered sequential removal of selected three or more clamps enables ordered sequential mixing of the three or more molding agent components. As the foam expands, it fills the bladder until it has compressed the internal aspect of the bladder against both the patient's head and the surface of the modeling spacer putty. As the foam further expands, excess pressure is avoided by permitting the foam to flow out of effluent tubes selectively provided in the bladder whereby the excess foam may flow into collection bags coupled with the bladder, or into an extra volume area provided in a self-contained bladder system of an embodiment. The effluent tubes may not be needed, however, when the amount of molding agent introduced into the helmet bladder matches the volume of the bladder as in the example embodiment. Pressure relief vents or holes are desirable in the bladder in accordance with the chemical formulation of the foam, for permitting excess gas or steam produced during the polymerization of the foam to be relieved as necessary or desired from the bladder while disposed in the gap between the patient's head and the orthosis.

The foam molding agent is then permitted to cure or harden in step 180 while the orthosis is in place on the patient's head. The orthosis is then selectively removed to permit final curing. Degassing or aeration of the foam molding agent may be desired or required to avoid excessive hardening in accordance with the formulation of foam. Degassing or aeration could be accomplished in accordance with the embodiment by removing inlet and/or outlet tubes of the bladder, or removing some or all of the internal aspect of the bladder.

After the curing of the molding agent in step 180, the orthosis is removed in step 190 from the patient's head together with the one or more modeling putty spacer members and elastic skull cap whereby the orthosis is provided with an inherent resultant internal contour which corresponds to the desired cranial form. The one or more pieces of modeling putty are discarded having served their purpose during the molding of providing temporary spacer members between the patient's head and the bladder containing the moldable material. Removal of the temporary spacer members results in one or more gaps between the patient's head and the bladder containing the moldable material defining one or more volumes into which the growth of the patient's skull may be directed.

As noted above, volumetric irregularity measurements or estimates of a patient's head volume are performed visually in one embodiment and, in another embodiment, by using associated scanning equipment. With reference FIGS. 2 and 3a-3d, a three dimensional computer image 200 of the head 202 and face 204 of an associated patient is illustrated including user-assigned landmarks for determination of midline and inferior extent for purposes of volume measurement. In the embodiment, the process is preferably initiated by capturing a complete surface scan of the patient's head and face. This scan may be performed with any conventional surface scanner which captures 3-dimensional data and is suitable for use on patients, such as for example optical projector scanners, laser scanners or other similar devices which do not pose a significant risk to the patient. The resulting captured image 200 may then selectively be converted into a three dimensional computer file representing the external contour of the patient's head 202.

In a preferred embodiment, the 3d camera/scanner is the 3dMD system (3dMD, Atlanta Ga.), a conventional surface scanner well known in the art, as it permits a complete surface scan of the head in milliseconds, avoiding any motion artifact during the image acquisition. This scan is digitally stored using any conventional 3d file format which is compatible with commercially available craniofacial image manipulation programs, such as Surgicase CMF (Materialise, Leuven, Belgium) or Vultus (3dMD, Atlanta, Ga.). These file formats can include STL, DXF, VRML, OBJ, 3DS and IGES formats. Alternately, free open source software such as NIH Image may be used for the volumetric calculation. Additionally, other types of scans can be utilized, such as 3d CT scans, MRI scans, or other scans which can provide 3-dimensional data about the craniofacial landmarks, in which case, the file formats typically utilized are DICOM files.

The image file is then imported into the manipulation software, the image 200 is then represented graphically, and landmarking is performed. The practitioner assigns landmark points within the image graphic file representing three dimensional coordinates, utilizing for example landmarking routines available in an associated software package. A minimum of 3 points are chosen to define the midline plane, and these points are saved in the 3d file. The simplest method for creation of the sagittal or midline plane 301 (FIG. 3c) of the file consists of defining a plane represented by the center of the nasofrontal junction or nasal radix 212, the lambda or apex of the lambdoidal suture or prominence thereof 213, and the columellar labial junction 214. The plane defined by these three points can be established within the patient's data set, and arbitrarily used as a functional midline. Additional or alternate landmarks can be utilized and would be known to practitioners skilled in the art, sharing the common goal with the current embodiment that an arbitrary midline plane 301 is defined for the purposes of volumetric analysis of the patient's head and face. The midline plane 301 can be determined or estimated by visual inspection of the patient's head from the top as well, such as in the example embodiment.

Figure 2:
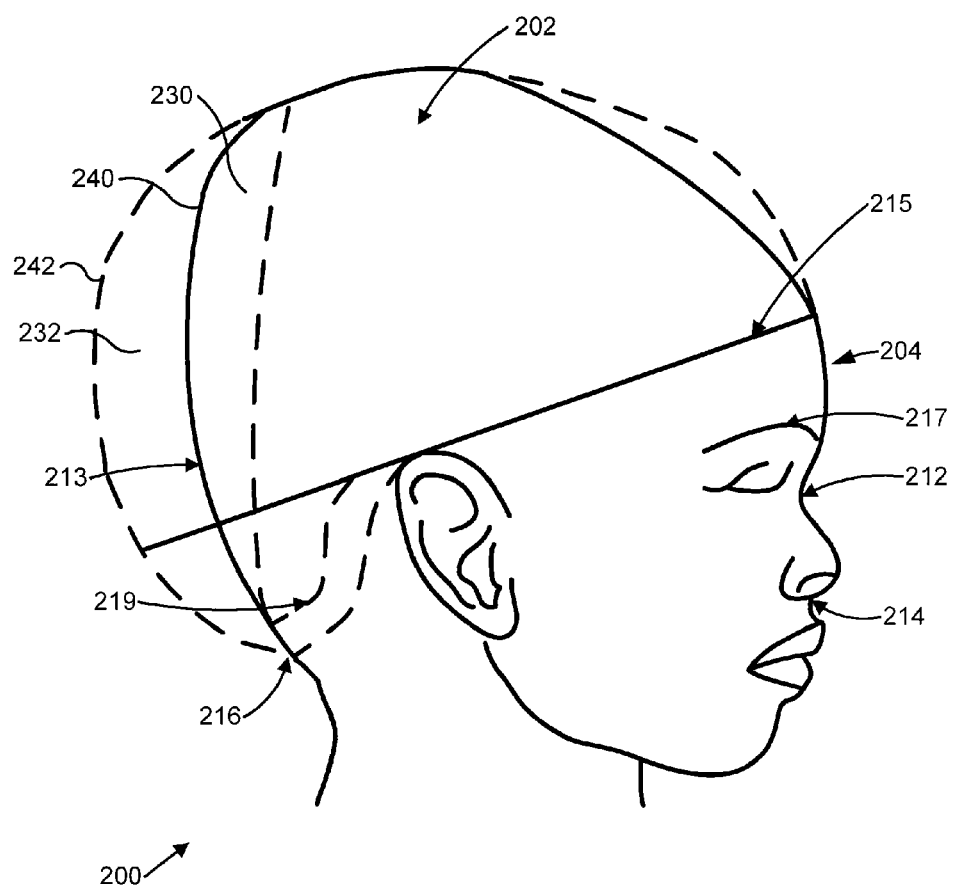
FIG. 2 illustrates an example three dimensional computer image of the head and face of an associated patient showing example assignment of landmarks for determination of midline and inferior extent of volume measurement.
Figure 3A:
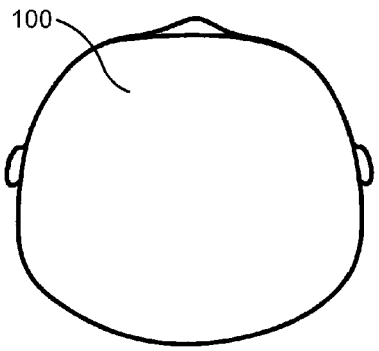
FIGS. 3a-3d illustrate graphical showings of the comparison of two sides of the patient's head in cross sectional view, permitting cranial volume calculation.
Figure 3C:
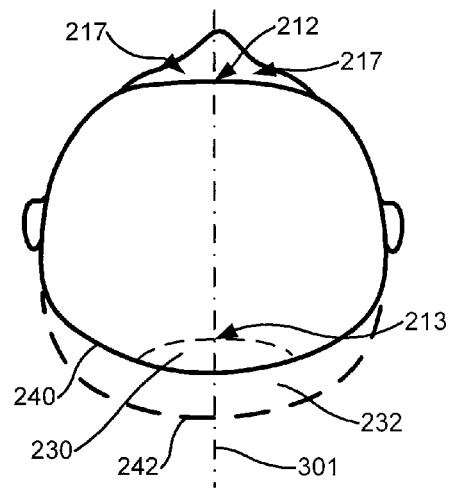
Figure 3B:
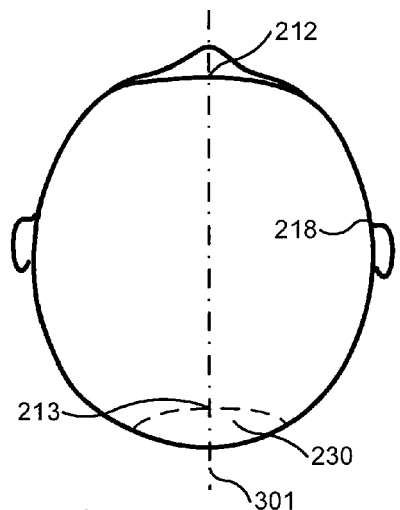
Figure 3D:
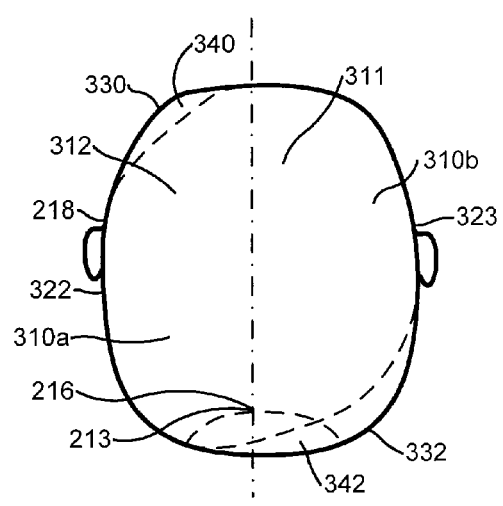

In a preferred embodiment, the inferior or caudal most extent of the planned volumetric calculation can be selected by establishing another plane 215 defined by the inferiormost point of desired contact on the posterior head 216, typically at the inferior hairline, and the supraorbital rim 217 bilaterally. This plane represents the inferior extent of the cranial volume to be calculated, and is landmarked and saved within the image manipulation software as was the midline plane 301 of the current embodiment. Alternately, landmarks could include the helical root of the external auricle 218, points along the posterior hairline, or other arbitrary cutoff point below which there is no planned helmet contact or treatment planned. As illustrated in FIG. 2, these landmarks are then selectively used to create imaginary meridians 219 across the cranial base to permit a more complex geometry to define the two volumes if so desired by the practitioner. These meridians are selectively used to define a cutoff below which no contact is desired, permitting a more accurate modeling of the planned cranial expansion volume.

In the example embodiment, the volumes 310a and 310b (FIG. 3d) representing the two sides of the head as defined by the surface of the head, the midline plane and the inferior plane or meridians of 219 are then calculated by using the associated software representing the two halves of the segmented data set. Once the volumes have been calculated or otherwise approximated, the lesser of the two volumes 311 is subtracted from the greater of the two volumes 312 with the difference representing the desired cranial expansion volume V.

Alternately, the outline of the greater volume contour 322 could be superimposed upon the outline of the lesser volume contour 323 graphically as shown at overlays 330 and 332, permitting the practitioner to see the areas of planned cranial expansion 340 and 342 necessary to create symmetry, and accommodate any further expansion which would be desirable as evident to a practitioner skilled in the art. This could include areas of additional planned expansion within the data set not defined by the simple volumetric difference. The volume calculation would then proceed as above. It is to be appreciated that the areas of planned cranial expansion 340 and 342 and approximate volumes thereof can be determined or estimated in an embodiment by visual inspection of the patient's head during an office visit.

The calculated or otherwise estimated volume differential or planned cranial expansion volume V, is then used to determine the appropriate weight of modeling putty to give the same volume as the planned cranial expansion volume. It is to be appreciated that small deviations in the assignment of midline do not compromise the final orthotic result substantially, and the present method allows for additional modifications of the calculated volume to made "on the fly" prior to foaming, delaying foaming until visual confirmation of adequate shape and symmetry is noted by the practitioner.

The calculated or otherwise estimated cranial expansion volume is then physically transferred to the patient's head in the form of one or more physical spacer members. Preferentially, this takes the form of a modeling putty-like material which can be applied to the patient's head. Given a known density (mass/volume) of modeling putty of Y and planned cranial expansion volume of Z, the weight of modeling putty needed for application to the patient is X, where X=Y×Z. In a preferred embodiment, Dow Corning 3179 Dilatant Compound, or other commercially available modeling clays such as Kleen-Klay, Chavant and Sculpey III can be utilized to create the areas of desired molding. However, any other material having the desired hand-formable and shape retaining properties can be used equivalently.

In the absence of a scanner in an alternative embodiment, the custom in situ molded orthotic is fabricated without the use of a scanner and volumetric calculation is made in person during an office visit, relying instead upon either a visual estimate of the practitioner fabricating the orthotic, or upon physical measurements taken from the patient. Transfer of the estimated volumetric difference to one or more physical spacer members such as the modeling putty would then proceed as in the preferred embodiment of the present invention. For example, the practitioner could visually detect an irregularly shaped portion 230 on the back of the patient's head such as shown for example in FIGS. 2, 3*b*, and 3*c*. In the embodiment using manual volumetric measurement and estimation, the practitioner would manually mold the modeling putty to fill the entire volume of the irregularly shaped portion 230 as well as fill additional volume 232 (FIG. 3*c*) between the back surface 240 of the patient's head and the end desired surface 242 of the patient's head.

A volume of modeling putty substantially equivalent to the difference in volume between the two sides is placed into a thin elastic cap within a pocket, and applied to the patient's head with the putty located over areas of deficient volume 230, 232, 340, 342. It is then manually manipulated into a shape which visually mirrors that of the larger or more normal side such as, for example, surface 242.

Figure 4:
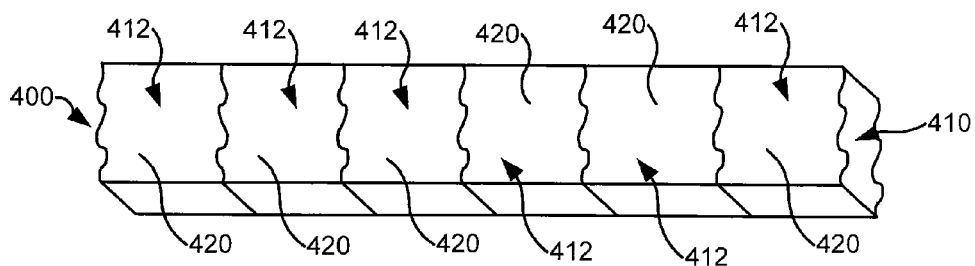
FIG. 4 is an illustration of a strip of modeling putty severable into easily metered portions for use as manually moldable spacer material in accordance with an example embodiment.

With reference next to FIG. 4, in a preferred embodiment, the modeling putty 400 is formed in a strip 410 and packaged in peel packs 412 in conveniently sized aliquots 420, such as 10 ml and 50 ml quantities. In this way, the practitioner would not have to weight out the putty in it raw form, but rather would simply open the indicated quantity of packages to approximate the desired target molding volume based on the density of the spacer material 400. This is advantageous as it simplifies the process 100 of fitting and forming the orthotic, minimizing the need to store separate containers of putty, weigh them out for each patient, and avoid hardening of the putty in its container. The practitioner would then compact the putty, rolling it in his hands until a "pancake" of material is created, prior to introducing it into the interior compartment of the elastic cap. Alternatively, the putty could be provided in bulk or in a lump quantity.

Figure 5:
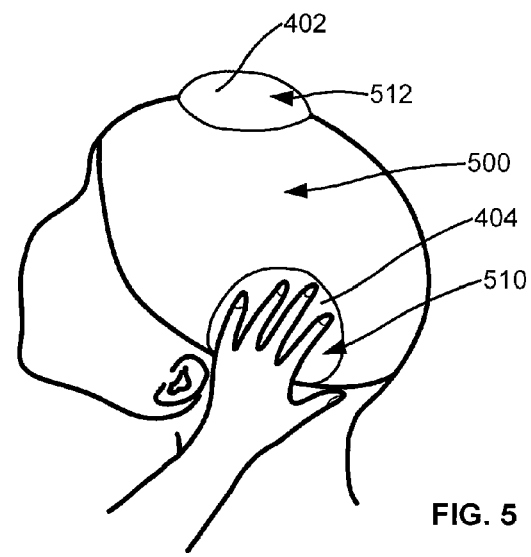
FIG. 5 is a graphical illustration of a head of a patient showing a method of manually applying metered portions of the modeling putty of FIG. 4 to irregularly-shaped skull portions of the patient's head in accordance with an embodiment.
Figure 6:
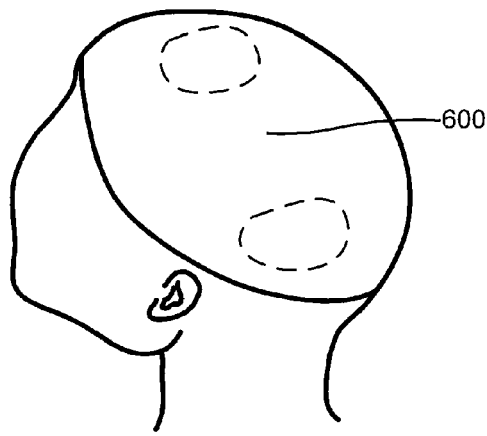
FIG. 6 is a graphical illustration of a head of a patient showing the modeling putty spacer members held in place by an elastic skull cap interface in accordance with an embodiment.
Figure 7:
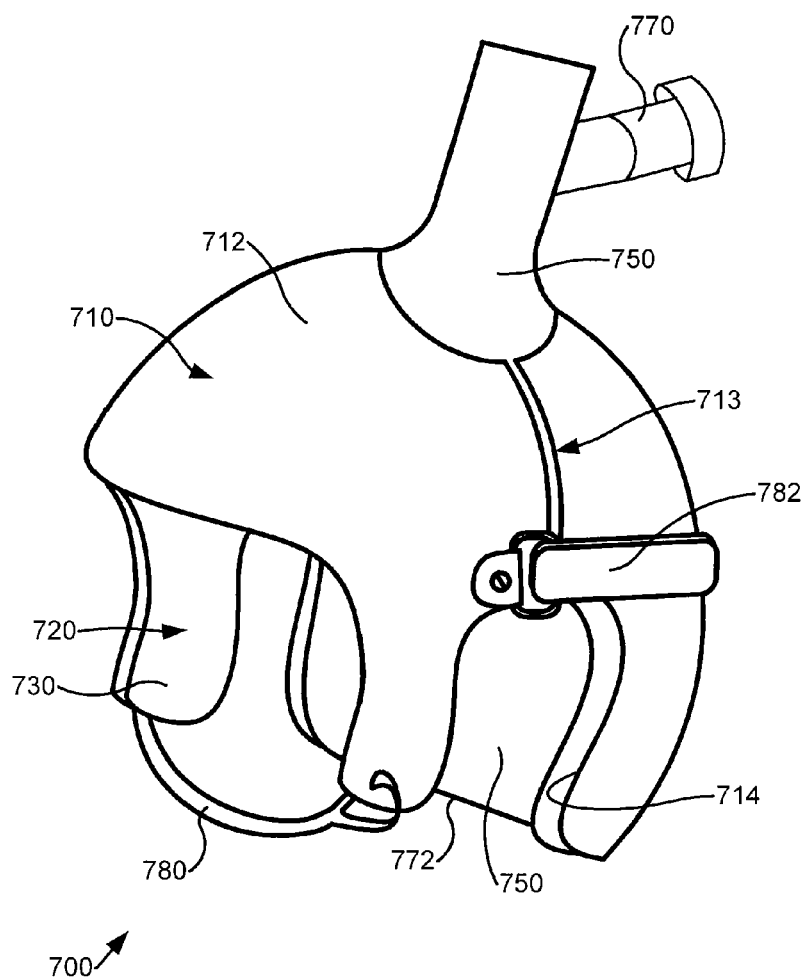
FIG. 7 is a perspective view of an orthotic system for cranial remodeling in accordance with an example embodiment.
Figure 8:
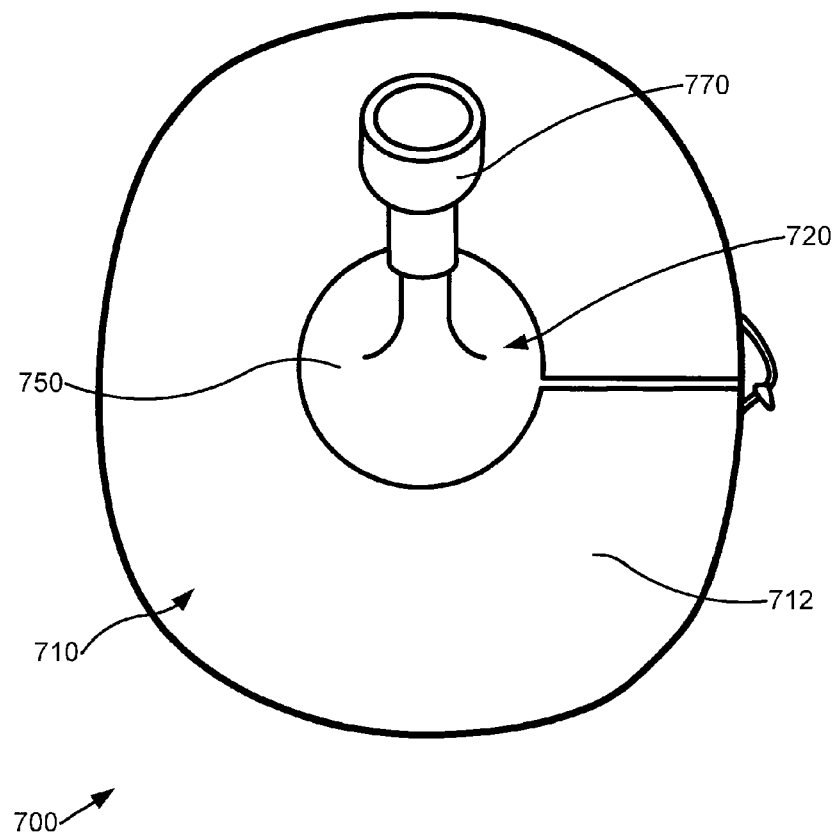
FIG. 8 is a top view of the orthotic system of FIG. 7 for cranial remodeling in accordance with an example embodiment.
Figure 9:
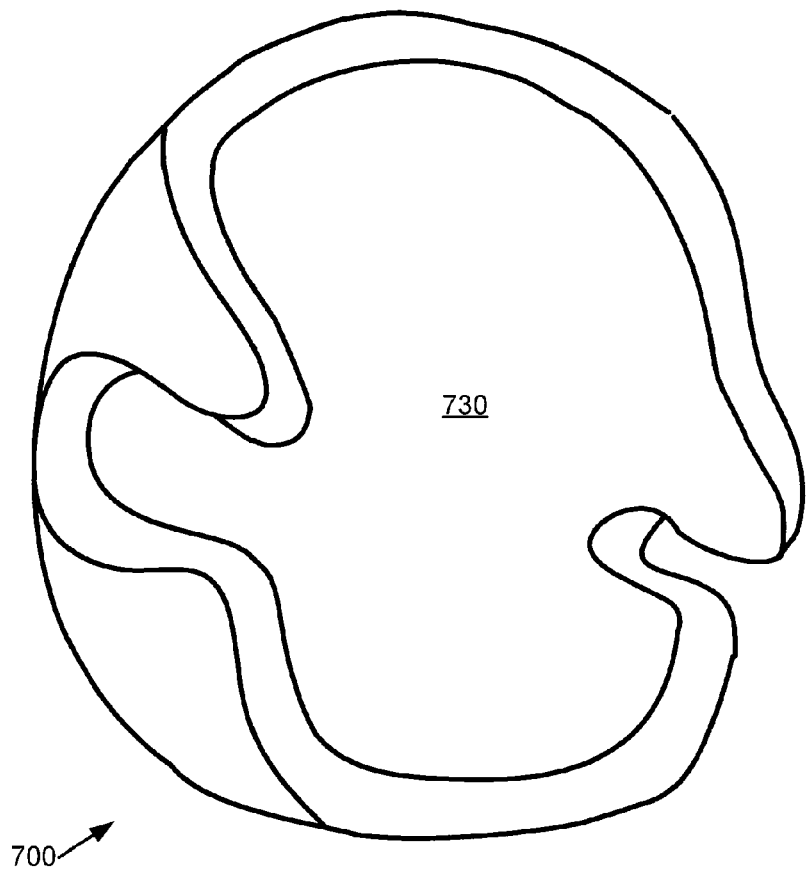
FIG. 9 is a bottom view of the orthotic system of FIGS. 7 and 8 for cranial remodeling in accordance with an example embodiment.

FIG. 5 illustrates an example of manual forming quantities of the spacer putty 402, 404 onto the head 500 of a patient or user at selected areas 510, 512. The quantity of modeling putty previously measured out is roughly distributed manually in the areas of planned cranial expansion. In FIG. 5, the selected areas 510, 512 are intended to illustrate the areas of planned cranial expansion 230, 232, 340, 342. The first putty spacer member 402 is illustrated in an unworked shape and the second spacer member 404 is illustrated being manually worked into the desired shape to fill cranial deficiencies at, for example, the selected area 510 and others as necessary or desired. In the example embodiment, an elastic skull cap 600 (FIG. 6) is used to hold the spacer putty members 402, 404 in place against the head of the patient and to provide a mechanical and thermal interface between the user's head and the bladder of the orthotic to be described below in greater detail. In its preferred form, the elastic skull cap 600 is formed of silicon and has an overall shape similar to a standard shower cap. However, other shapes and materials may be used as necessary or desired and having sufficient properties to adequately insulate against heat generated by the curing process and to ensure that the spacer putty members are firmly held against the patient's head without slippage or movement as the expandable molding material of the helmet orthotic is positioned and permitted to cure. In one embodiment, the spacer putty members 402, 404 are placed within a suitably formed pocket of the cap garment, roughly distributing the volume manually in the areas of planned cranial expansion 230, 232, 340, 342. In another embodiment, the putty spacer members 402, 404 are located on the patient's head and then the cap 600 is placed upon the patient's head, covering and holding the spacer members 402, 404 in place. The remainder of the modeling is carried out by manually manipulating the spacer material putty 400 until it is symmetric with the contralateral side (FIGS. 5 and 6). It is to be appreciated that the manual manipulation of the spacer material putty 402, 404 is not necessarily limited to manipulation on the deficient side, but additional modeling putty can be aggregated to other areas of desired molding, as determined by the practitioner. Once symmetrically molded and all areas of desired relief having been filled in with putty, the helmet orthotic 700 (FIG. 7) is then placed upon the patient's head and secured with the chin strap 780 and fastener strap 782. It is important that while placing the helmet orthosis over the cap, distortion of the putty is avoided to maintain a faithful representation of the desired contour after foaming the device in situ. The orthotic is then ready for in situ foaming, creating a direct negative cast of the preferred cranial expansion shape without the creation of an intermediated positive mannequin head.

In an alternative embodiment, the modeling putty could be replaced by another physical spacer material, such as a bag filled with fine beads, grains, or other contourable substance. This could then be subjected to a vacuum after molding, permitting definition of the desired contour. There are numerous alternative materials and methods for application of physical spacer material for subsequent in situ molding which would be obvious to the practitioner which are not enumerated herein.

As illustrated in a preferred example embodiment in FIGS. 7-10, an orthotic system 700 is shown for inducing directed growth of an irregularly-shaped associated skull of an associated user having a regularly-shaped skull portion and at least one irregularly-shaped skull portion recessed relative to the regularly-shaped skull portion. The orthotic system 700 comprises a headpiece 710 having an outer wall 712 and an inner wall 714, and a resilient material 720 disposed on the inner wall 714 of the headpiece 710. As shown, the inner wall 714 is shaped to receive a head of an associated user with a suitably sized gap therebetween to be easily placed onto the user's head with the resilient material received in the headpiece. To further ease installation, the headpiece 710 is formed of a plastic material and may be provided with a hinge at a selected location or a vertical slit 713 as illustrated to permit the device to be opened slightly for receiving the body part such as an arm, leg or head therein. In the example embodiment, the resilient material 720 has a first surface 730 formed to substantially correspond to a shape of the head of the associated user by molding the resilient material in situ between the head of the associated user and the inner wall of the headpiece. The first surface 730 defines a contact wall surface area 732 (FIG. 10) positioned to abut and limit growth of the regularly-shaped skull portion of the associated user, and at least one target wall surface area 734, 736 positioned to define a volume 735, 737 between the at least one irregularly-shaped skull portion of the associated user and the at least one target wall surface area 734, 736 into which the growth of the skull may be directed.

Figure 10:
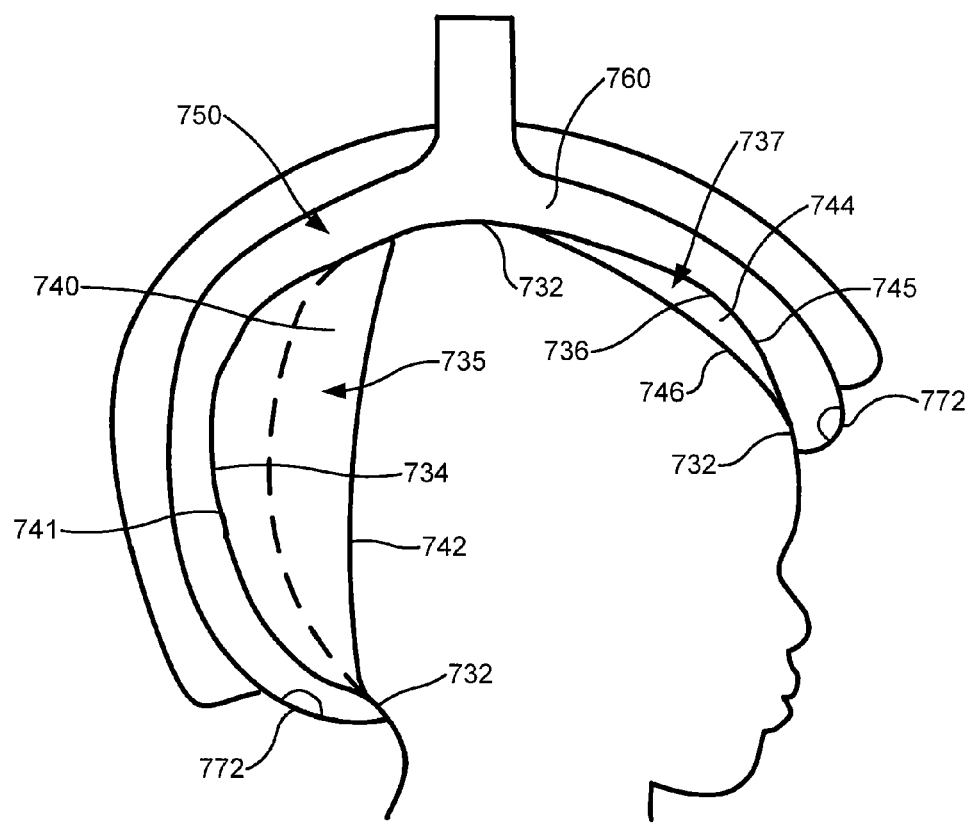
FIG. 10 is a cross-sectional view of the orthotic system of FIGS. 7-9 in situ during molding and curing of molding agent in bladder; and, FIG. 11 a bottom view of an alternative embodiment of the orthotic helmet including a multi-part bladder holding which the bladder system is ready for mixing and activation.

As shown best in cross-sectional view in FIG. 10, the orthotic system 700 of the example embodiment further comprises at least one spacer member 740, 744 (two are illustrated in the general positions of the spacer members 402, 404 illustrated in FIGS. 5 and 6) selectively received in the volumes 735, 737 between the at least one irregularly-shaped skull portion of the associated user and the at least one target wall surface area 734, 736. As illustrated, the first of the at least one spacer member 740 has opposite first 741 and second 742 sides wherein the first side has a shape corresponding to the at least one irregularly-shaped skull portion of the associated user and the second side has a shape corresponding to the at least one target wall surface. Similarly, the other spacer member illustrated 744 has opposite first 745 and second 746 sides wherein the first side has a shape corresponding to the at least one irregularly-shaped skull portion of the associated user and the second side has a shape corresponding to the at least one target wall surface. It is to be appreciated that the spacer members 740, 744 are selectively retained, such as shown best in FIG. 10, in the volumes 735, 737 between the at least one irregularly-shaped skull portion of the associated user and the at least one target wall surface area during the molding of the resilient member in situ between the head of the associated user and the inner wall of the headpiece 710. The one or more spacer members 740, 744 are selectively removable from between the at least one irregularly-shaped skull portion of the associated user and the at least one target wall surface thereby defining one or more volumes into which the growth of the skull may be directed. During use of the device, the volumes are empty or otherwise filled by atmosphere.

With continued reference to FIGS. 7-10, the resilient material 720 comprises an outer flexible bladder 750 and a molding agent 760 contained within the flexible bladder 750. In the example embodiment, the molding agent 760 has desirable properties including for example a first stage being flowable relative to the bladder 750 prior to curing and having a second stage being hardened in situ during curing on the head of the associated user. Preferably, the molding agent 760 comprises an expandable foam. The molding agent 760 of the example embodiment hardens exothermally between the first and second stages. In the example embodiment, since the molding agent is exothermic during fitting of the device, the skull cap interface 600 functions not only to hold the putty spacer members in place relative to the patient's head, but also to provide a selected level of thermal resistance for reducing the transfer of energy to the patient's head released from the chemical reaction within the bladder. Accordingly, in one form the bladder is made of a silicone material selected or otherwise designed to be impermeable to the foaming agent 760. The overall configuration of the bladder is selected to provide an excess of space for introduction of a self expanding foaming agent. The interior of the bladder is shaped as shown to permit a free flow of the foaming agent to permit complete penetration of the space between the shell and the patient's head. The outer flexible bladder comprises a fluid port 770 configured to selectively communicate the expandable foam into the bladder from an operatively associated source (not shown), and one or vents 772 configured to selectively release pressure from within the bladder such as caused, for example, by gases or the like generated during the exothermal reaction of the molding agent 760 during the hardening between the first and second stages of the molding agent. In one embodiment, although only several vents are shown in the drawings for ease of reference, the vents or holes are formed in the bladder using a "bed of nails" technique wherein a plurality of spaced apart pins or needles are arranged on a form movable relative to the bladder to simultaneously pierce the bladder at plural locations forming a corresponding set of plural vent holes therein. In this way, gas relief is provided and venting repeatability is enhanced during manufacture. The port coupling 770 may be any suitable fluid tight coupling such as any of the plastic couplers currently available or any of those currently used in the medical arts or others to be developed.

The foam or equivalent molding agent is then activated and injected or otherwise introduced within the bladder system 750 while the orthosis 700 is fastened in place on the head of an associated user using for example a chin strap 780 and fastener 782 to hold the helmet 710 in place while the foam 760 is being injected. The foam expands to make contact with the entire cranium and the prominences created by the modeling putty. It is to be appreciated that the two-part foam components are mixed as necessary or desired such as, for example, by manual mixing or by sequentially rupturing and mixing ampules or cells of a packet having compartments holding the molding agent.

In a preferred embodiment, the foaming agent is comprised of a mixture of polymeric diphenylmethane diisocyanate (Iso, MDI), polyol (polyether glycerol, polyether glycol), and catalyst (33% triethylenediamine (TEDA), 66% dipropylene glycol (DPG)), mixed in proportions to create a foam with a majority of open cells. In the current embodiment, a soft foam can be created with a density of 5.2 lb/cubic ft. This mixture requires 1.5 g catalyst and 43 g iso per 100 g polyol, resulting in a foam with sufficient softness to minimize the risk of pressure points. It is known to practitioners in the art that increasing concentrations of Iso to Polyol result in foams of increasing density and firmness. The practitioner can modify these proportions to achieve a foam of distinct firmness for differing clinical requirements.

Other embodiments of the flowable foam of the present invention could comprise a 1 part polyurethane foam which can be delivered in an aerosol-type can, or a 2 part polyurethane foam with self-mixing delivery system which can be delivered via 2 cans or pressure vessels with a mixing manifold and attachment for connecting the foam delivery system with the inlet tubes or the cranial orthotic. The effluent tubes permit the egress of the excess material to avoid unnecessary pressure against the infant's head, and the helmet is then permitted to cure in place.

The foaming components are in the example embodiment contained within a separate bag provided with a connector selected for operative fluid tight attachment to the port coupling 770 of the helmet bladder 750. The foam precursor components could be separated by external clips as in the "Liquid Sunmate Foam In Place Seating Bag Pack" as marketed by Dynamic Systems (Leicester, N.C.). In yet another alternate embodiment, the components could also be mixed in an open container, then transferred to a bag or similar container for introduction to the bladder of the helmet.

In yet another alternate embodiment, the introduction of the foaming components could be accomplished utilizing a polyethylene bag of a design commonly used in IV fluid bags. The secondary foam components could be injected with commercially available leak-proof connectors as are used to connect tubing circuits to the IV bag. The components would then be mixed in the IV bag and the foam would enter the bladder as in previous iterations of the current invention. This method also has the advantage of utilizing the bag as an overflow receptacle for excess foam generated, and can be used to capture gases venting from the bladder.

Whether the practitioner adopts an external foaming system, or relies upon internal compartments of the bladder in accordance with an alternative embodiment described below to permit foam generation, the subsequent management proceeds in a similar manner. The device 700 is removed after foaming and initial curing, the cap 600 with the putty spacer members 400 is removed, the tubes if any or protruding bladder portions such as the fill vent near the port coupling 770 and other portions if any are trimmed off as necessary, and the portion of the bladder in contact with the patient is removed, perforated and/or aerated to avoid excessive hardening of the foam if necessary given the specific composition of the foam. Thereafter, the orthotic system 700 is then ready for use in cranial molding during head growth of the patient.

Figure 11:
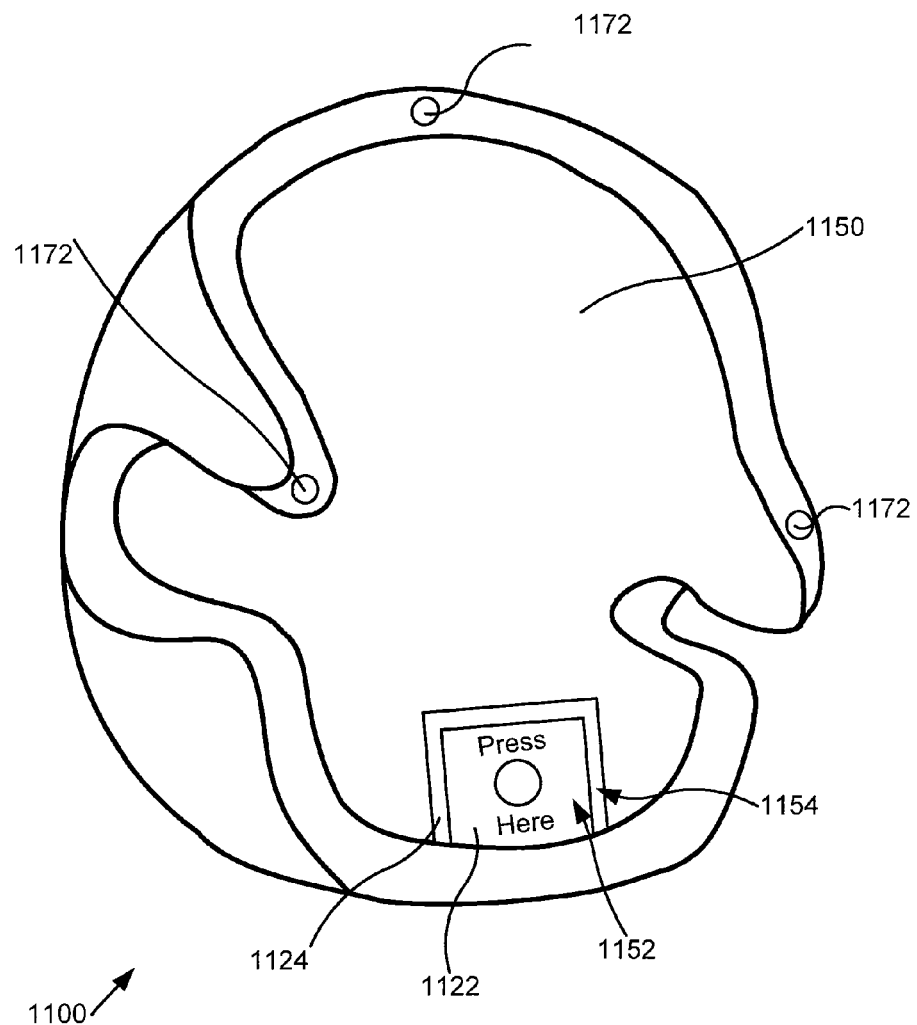

In a further example embodiment as illustrated in FIG. 11, the foam components are contained in cells 1152 or ampules 1154 within the bladder 1150 of the helmet 1100, permitting the cells or ampules to rupture with manually applied pressure, mixing the precursors and generating the foam within the bladder. This permits the practitioner to create the in situ molded orthotic without having to deliver the foam components via external delivery systems. Preferentially, this polyurethane foam comprises a two-part foam with a majority of open cells. In a further preferred embodiment, the foam consists of a polyurethane foam which does not result in excessive heat or pressure generation.

In the example embodiment shown in FIG. 11, it may be desirable to the practitioner to have the foaming components contained within the flexible plastic liner bladder, in integrated interior compartments 1152, 1154 each containing the precursor agents for the foaming process. The components are stable for storage and transportation in their respective interior cells until the seal between the compartments is broken by squeezing or applying pressure to the compartments. Then, the components are mixed and the foaming process progresses as previously described. The bladder could be comprised of a laminated plastic sheet system analogous to the "foam in bag" design such as marketed by the Sealed Air Corporation as INSTAPAK QUICK™ foam packaging.

In this iteration exemplified in FIG. 11, the bladder 1150 preferably comprises a multilaminate 1122 of plastic sheeting with areas of frangible seals 1124 in areas of desired rupture of the foam precursor components. This design relies upon creation of an inner bilayer laminate of plastic film separated by internal seals which are created by printing or applying a layer of releasing agent between the inner laminates. Individual cells are defined by the pattern of releasing agent, permitting the creation of separation of the foam precursors. These seals are created to permit the application of external pressure to the cells containing the foam precursors such that the frangible seals rupture and permit admixture of the foaming precursors. The subsequent pressure and heat generated by the rising foam ruptures the secondary seal and permits the introduction of the expanding foam to the internal aspect of the helmet bladder. FIG. 11 illustrates the manual activation of these foam precursors by rupturing the seals between the internal cells of the example embodiment.

In a further example embodiment, multi-compartmented, laminated plastic package in which a heat-sensitive internal frangible seal can be broken as the internal temperature rises above a pre-calculated cutoff temperature are well suited to creation of the custom cranial orthotic of the present examples. In these embodiments, the components are warmed sufficiently to result in rupture of the frangible seal, mixing the precursors and generation of said flowable foam of the current embodiment. The foam may be warmed in any number of conventional modalities, such as microwaving, immersing the helmet in warm water, or the like as necessary or desired. Either of these examples of prior art provide a convenient method for delivering foaming components in their native, stable form within the helmet bladder, to permit rupturing the seal and internal mixing of the foam components. The in situ molding of the device would then proceed as previously described.

In yet another example embodiment, the orthotic system comprises a flexible shell with a silicone bladder containing a plurality of inlet and outlet tubes to permit instilling the foaming agent. These tubes are located to permit easy instillation and outflow of the foaming agent. This permits a free flow of the foaming agent to permit complete penetration of the space between the shell and the patient's head.

In an alternative embodiment of the present invention, the bladder can be composed of a flexible plastic liner or bag, with excess capacity, to allow the foaming process to proceed without having to utilize the inlet and outlet tubes, but rather introducing the premixed foaming agent directly into the bladder without the tubing arrangement.

In an alternative embodiment to the bladder system, the inlet tube could be attached to a syringe or other closed system for delivering the two part foam, or could be attached to an separate plastic bag with a connector. Within the bag, the two foam components could be contained by rupturable sealed cells which could be compressed at the time of foaming, breaking the seal and mixing the components. They would then be introduced via the inlet port by squeezing the bag until the components enter the bladder, initiating the custom molding process as described in the present invention.

Alternatively, the foam can be introduced by piercing a membrane affixed to an entry port to the liner, utilizing a type of connection typically used to sterilely attach intravenous tubing to a plastic bag of intravenous fluid. This approach has the advantage of permitting the components to be mixed in a clear external bag, then once the connection has been established with the bladder or liner, the plastic bag can then be used to contain the excess foam as it is generated. In a system of this design, the plastic bag would be capable of containing a volume of excess foam greater than the predicted maximum volume of foam needed to fabricate a helmet orthotic, thereby using the excess volume of the bag as an integral effluent container, thereby avoiding the necessity of having separate inflow and outflow containers.

The expansion of the foam may cause the helmet to be displaced during the foaming process, such that it may be desirable to utilize spacers to assure that the helmet is centrically placed and there is adequate space in all axes to permit an even flow of the foam. These could take the form of blocks, dowels, or other geometric shapes which could be affixed to the internal aspect of the helmet to assure this centric relationship. These would be preferentially formed of a similar density foam to that utilized in the foaming process, and would either be pre-applied to strategic support points prior to foaming, or could be incorporated in the internal aspect of the bladder to become integrated into a monolithic foam liner. These could also come as additional supports with self adhesive strips for further custom fitting prior to the foaming process.

The spacers of the current embodiment would be of a similar height to the maximum desired molding foam depth to permit establishment of a uniform distance of the helmet shell or shell from the patient's scalp and face, ensuring that the foam will flow freely around the head and provide a relatively uniform base padding in all quadrants of the interior of the orthotic. This method has the advantage of avoiding areas of poor padding, or distortion of the planned fit of the helmet due to excess pressure from the expanding foam which could cause the helmet orthotic to migrate or move during the foaming and curing process with a detrimental affect upon the fit of the device or upon subsequent cranial molding.

In yet another embodiment, it may be desirable to the practitioner to include a thermometer within the internal aspect of the device to ensure that the temperatures do not rise to levels which could injure the patients scalp during the exothermic portion of the foaming process. This would preferentially comprise a disposable colorimetric type of temperature sensor commercially available in the food service and medical industries. The thermometer would alert the practitioner if excess temperature were generated, and could also serve to document adequate heat generation to assure uniformity and quality of the foaming process.

These specific embodiments described are meant to be illustrative and not limiting in regard to the scope of the present invention. It is understood that further modifications and other embodiments will be evident to one skilled in the art as deriving from the current invention and therefore fall under the scope of the claims as presented in this patent application.

The invention claimed is:

1. An orthotic system for inducing directed growth of an irregularly-shaped associated skull of an associated user having a regularly-shaped skull portion and at least one irregularly-shaped skull portion recessed relative to the regularly-shaped skull portion, the orthotic system comprising:
a headpiece having an outer wall and an inner wall, the inner wall being shaped to receive a head of an associated user;
a resilient material disposed on the inner wall of the headpiece, the resilient material having a first surface found to substantially correspond to a shape of the head of the associated user by molding the resilient material in situ between the head of the associated user and the inner wall of the headpiece, the first surface defining i) a contact wall surface area positioned to abut and limit growth of the regularly-shaped skull portion of the associated user, and ii) at least one target wall surface area positioned to define a volume between the at least one irregularly-shaped skull portion of the associated user and the at least one target wall surface area into which the growth of the skull may be directed; and,
at least one spacer member comprising a manually moldable shape retaining material selectively received in the volume between the at least one irregularly-shaped skull portion of the associated user and the at least one target wall surface area, the at least one spacer member having opposite first and second sides wherein the first side has a shape corresponding to the at least one irregularly-shaped skull portion of the associated user formed by molding the material into the at least one irregularly-shaped skull portion recessed relative to the regularly-shaped skull portion, and wherein the second side has a shape corresponding to the at least one target wall surface formed by molding the second side of the material to substantially match the regularly-shaped skull portions surrounding the irregularly-shaped skull portion;
wherein the resilient material comprises a molding agent having a first stage being selectively flowable in an associated bladder disposed in a space between i) the inner wall of the headpiece and ii) the head of the associated user and the second side of the at least one spacer member, and a second stage being hardened in situ on the head of the associated user, the molding agent hardening between the first and second stages thereby defining, in the second stage, the contact wall surface area and the target wall surface area.

2. The orthotic system according to claim 1, wherein:
the at least one spacer member comprises a shape retaining putty material capable of being modeled by hand; and,
the resilient material is a hardened cured foam.

3. The orthotic system according to claim 1, wherein the at least one spacer member is selectively retained in the volume between the at least one irregularly-shaped skull portion of the associated user and the at least one target wall surface area during the molding of the resilient member in situ between the head of the associated user and the inner wall of the headpiece.

4. The orthotic system according to claim 1, wherein the at least one spacer member is selectively removed from between the at least one irregularly-shaped skull portion of the associated user and the at least one target wall surface thereby defining the volume into which the growth of the skull may be directed.

5. An orthotic system for inducing directed growth of an irregularly-shaped associated skull of an associated user having a regularly-shaped skull portion and at least one irregularly-shaped skull portion recessed relative to the regularly-shaped skull portion, the orthotic system comprising:
a headpiece having an outer wall and an inner wall, the inner wall being shaped to receive a head of an associated user;
a resilient material disposed on the inner wall of the headpiece, the resilient material having a first surface formed to substantially correspond to a shape of the head of the associated user by molding the resilient material in situ between the head of the associated user and the inner wall of the headpiece, the first surface defining i) a contact wall surface area positioned to abut and limit growth of the regularly-shaped skull portion of the associated user, and ii) at least one target wall surface area positioned to define a volume between the at least one irregularly-shaped skull portion of the associated user and the at least one target wall surface area into which the growth of the skull may be directed; and,
at least one spacer member comprising a manually moldable shape retaining material selectively received in the volume between the at least one irregularly-shaped skull portion of the associated user and the at least one target wall surface area, the at least one spacer member having opposite first and second sides wherein the first side has a shape corresponding to the at least one irregularly-shaped skull portion of the associated user formed by molding the material into the at least one irregularly-shaped skull portion recessed relative to the regularly-shaped skull portion, and wherein the second side has a shape corresponding to the at least one target wall surface formed by molding the second side of the material to substantially match the regularly-shaped skull portions surrounding the irregularly-shaped skull portion, wherein the resilient material comprises:
- an outer flexible bladder; and,
- a molding agent in the flexible bladder, the molding agent having a first stage being flowable relative to the bladder and having a second stage being hardened in situ on the head of the associated user, the molding agent exothermally hardening between the first and second stages.

6. The orthotic system according to claim 5, wherein:
the molding agent comprises an expandable foam; and,
the outer flexible bladder comprises a fluid port configured to selectively communicate the expandable foam into the bladder.

7. The orthotic system according to claim 6, wherein:
the molding agent comprises an expandable foam comprising a mixture of polymeric diphenylmethane diisocyanate, polyol, and a catalyst mixed in selected proportions to create a foam with a majority of open cells; and,
the outer flexible bladder comprises a vent configured to selectively release pressure from within the bladder during the exothermal hardening between the first and second stages of the molding agent.

8. An orthotic device for modifying skull shape in a growing patient, said device comprising:
- a shell of a predetermined form and size which substantially encircles a head of an associated infant patient's head;
- an inflatable bladder connected with an interior of said shell;
- a molding agent selectively introduced into the bladder in a flowable condition prior to molding of the agent, said molding agent being capable of curing and hardening while the orthotic device is in place on the associated infant patient's head; and,
- a manually moldable shape-retaining spacer material selectively positioned relative to the bladder and patient's head to define, during the curing and hardening of the agent, a desired inner surface area on the bladder opposite the patient's head in accordance with a manual molding of the shape-retaining spacer material to form a negative of the desired inner surface area, and to create the gap when the shape-retaining spacer material is selectively removed from the orthotic device after the curing and hardening.

9. The orthotic device of claim 8, wherein said device comprises a bladder and molding agent of sufficient rigidity to result in cranial molding without said shell.

10. The orthotic device of claim 8, further comprising one or more joints of discontinuity in said shell to permit removal and replacement of the shell relative to the patient's head.

11. The orthotic device of claim 8, wherein the shell comprises a hemisphere, a truncated sphere, or a convex band, of sufficient size to accommodate an adequate volume of said molding agent to permit desired cranial molding.

12. The orthotic of claim 8, wherein said shell is formed of a material selected from the group consisting of: high impact thermoplastic, polycarbonate, polyethylene, polypropylene, polyurethane, polyamide, cellular plastic, rubber, carbon fiber composite or fiberglass.

13. The orthotic device of claim 8, wherein said bladder comprises a rectangular, cylindrical or toroidally shaped, expansile bag of predetermined size and shape corresponding to the shape of the shell, suitable for attachment with the interior of the shell.

14. The orthotic device of claim 8, wherein said bladder comprises a port or chamber for introduction of an expandable foam as the molding agent into the bladder.

15. The orthotic device according to claim 8, wherein said bladder is formed of a material comprised of at least one polymer selected from the group consisting of: silicone membrane, polyisoprene, polyurethane, viscoelastic polymer, or polymeric plastic sheet or film.

16. The orthotic device of claim 8, wherein said bladder is a dip molded bladder.

17. The orthotic device of claim 8, wherein said bladder is a spray molded bladder.

18. The orthotic device of claim 8, wherein said bladder comprises individual separate cells or pouches with frangible seals between the pouches suitable for maintaining foam precursor components of the molding agent in their stable, native form in the individual separate cells.

19. The orthotic device of claim 8, wherein said bladder defines an aperture configured to vent excess steam or foam produced by a polymerization reaction of the molding agent.

20. The orthotic device of claim 8, wherein said bladder comprises at least one rupturable ampule or bag containing at least one of the precursor materials of polyethylene, polypropylene, polyamide, polyester, polyvinylidene chloride, ethylene/vinyl alcohol copolymer, silicone elastomer, polyisoprene, polyurethane or combinations of two or more thereof; amorphous polyethylene teraphthalate copolymer, ethylene/vinyl acetate copolymer, or any combination thereof.

21. A method for modifying skull shape in an associated growing patient, the method comprising:
- providing an orthotic device selectively wearable on the head of the associated patient, the device comprising a material which is molded in situ upon the head of the associated patient during a molding process, said device defining a gap between the device and the patient's head in at least one location formed by areas of physical spacer placement during the molding process, the device having an inner surface defining at least one area configured for non-contact with the head of the associated patient completely surrounded by an area configured for contact with the head of the associated patient;
- constraining, during a selected time period by the orthotic device, cranial growth in the area configured for contact;
- permitting, during the selected time period, the cranial growth by expansion of the head of the associated patient in the areas configured for non-contact by the orthotic device formed by areas of physical spacer placement during the molding process.

22. An orthotic system comprising:
- a shell member having an outer wall and an inner wall, the inner wall being shaped to receive a body part of an associated user;
- a resilient material in an associated bladder disposed on the inner wall of the shell member, the resilient material having a first surface formed to substantially correspond to a shape of the body part of the associated user by molding the resilient material in situ in the associated bladder disposed between the body part of the associated user and the inner wall of the shell member, the first surface defining a contact wall surface area positioned to abut and limit movement of the body part of the associated user, wherein the first surface defines at least one target wall surface area positioned to define a volume between the body part of the associated user and the at least one target wall surface area into which the body part may move; and, at least one spacer member comprising a manually moldable shape-retaining material selectively received in the volume between the body part of the associated user and the at least one target wall surface area, the at least one spacer member having opposite first and second sides wherein the first side has a shape molded to correspond to the body part of the associated user and the second side has a desired shape being manually molded to correspond to the at least one target wall surface.

23. The orthotic system according to claim 22, wherein the at least one spacer member is selectively retained in the volume between the body part of the associated user and the at least one target wall surface area during the molding of the resilient member in situ between the body part of the associated user and the inner wall of the shell member.

24. The orthotic system according to claim 23, wherein the at least one spacer member is selectively removed from between the body part of the associated user and the at least one target wall surface thereby defining the volume into which the movement of the body part relative to the shell may be permitted.

25. An orthotic system comprising:
a shell member having an outer wall and an inner wall, the inner wall being shaped to receive a body part of an associated user;
a resilient material disposed on the inner wall of the shell member, the resilient material having a first surface formed to substantially correspond to a shape of the body part of the associated user by molding the resilient material in situ between the body part of the associated user and the inner wall of the shell member, the first surface defining a contact wall surface area positioned to abut and limit movement of the body part of the associated user, wherein the first surface defines at least one target wall surface area positioned to define a volume between the body part of the associated user and the at least one target wall surface area into which the body part may move; and,
at least one spacer member comprising a manually moldable shape-retaining material selectively received in the volume between the body part of the associated user and the at least one target wall surface area, the at least one spacer member having opposite first and second sides wherein the first side has a shape molded to correspond to the body part of the associated user and the second side has a desired shape being manually molded to correspond to the at least one target wall surface,
wherein the resilient material comprises:
an outer flexible bladder; and,
a molding agent in the flexible bladder, the molding agent having a first stage being flowable relative to the bladder and having a second stage being hardened in situ on the body part of the associated user, the molding agent exothermally hardening between the first and second stages.

26. The orthotic system according to claim 25, wherein:
the molding agent comprises an expandable foam; and,
the outer flexible bladder comprises a fluid port configured to selectively communicate the expandable foam into the bladder.

27. The orthotic system according to claim 26, wherein:
the outer flexible bladder comprises a vent configured to selectively release pressure from within the bladder during the exothermal hardening between the first and second stages of the molding agent.

28. An orthotic device for immobilizing a body part of an associated patient, said device comprising:
an outer shell selectively openable to receive the body part of an associated patient;
a material selectively disposed between the outer shell and the body part of an associated patient, the material being molded in situ upon the body part of the patient;
a shell of a predetermined form and size which substantially encircles the body part of an associated patient;
a bladder connected with an interior of said shell; and,
a molding agent selectively introduced into the bladder in a flowable condition, said molding agent being capable of curing and hardening while the orthotic device is in place on the body part of the associated patient.

29. The orthotic device of claim 28, further comprising one or more joints of discontinuity in said shell to permit removal and replacement on the body part of the patient.

30. The orthotic of claim 29, wherein said shell is formed of a material selected from the group consisting of: high impact thermoplastic, polycarbonate, polyethylene, polypropylene, polyurethane, polyamide, cellular plastic, rubber, carbon fiber composite or fiberglass.

31. The orthotic device of claim 28, wherein said bladder comprises a rectangular, cylindrical or toroidally shaped, expansile bag of predetermined size and shape corresponding to the shape of the shell, suitable for attachment to the inner aspect of the shell.

32. The orthotic device of claim 28, wherein said bladder comprises a port or chamber for introduction of the molding agent.

33. The orthotic device according to claim 28, wherein said bladder is formed of a material comprised of at least one polymer selected from the group consisting of: silicone membrane, polyisoprene, polyurethane, viscoelastic polymer, or polymeric plastic sheet or film.

34. The orthotic device of claim 28, wherein said bladder is a dip molded bladder.

35. The orthotic device of claim 28, wherein said bladder is a spray molded bladder.

36. The orthotic device of claim 28, wherein said bladder comprises individual separate cells or pouches with frangible seals between the pouches suitable for maintaining foam precursor components of the molding agent in a stable, native form in the individual separate cells.

37. The orthotic device of claim 28, wherein said bladder defines an aperture configured to vent excess steam or foam produced by a polymerization reaction of the molding agent.

38. The orthotic device of claim 28, wherein said bladder comprises at least one rupturable ampule or bag containing at least one of the precursor materials of polyethylene, polypropylene, polyamide, polyester, polyvinylidene chloride, ethylene/vinyl alcohol copolymer, silicone elastomer, polyisoprene, polyurethane or combinations of two or more thereof; amorphous polyethylene teraphthalate copolymer, ethylene/vinyl acetate copolymer, or any combination thereof.

39. A method of making an orthotic device, the method comprising:
  providing an orthotic system comprising:
    a shell member having an outer wall and an inner wall, the inner wall being shaped to receive a selected body part of an associated user; and,
    a resilient material disposed on the inner wall of the shell member, the resilient material having a first surface formed to substantially correspond to a shape of the body part of the associated user, the first surface defining a contact wall surface area positioned to abut and limit movement of the body part of the associated user;
  providing a manually moldable shape-retaining spacer material;
  modeling the spacer material on the selected body part of the associated user to conform on a first side to a shape of the selected body part of the associated user and to conform on a second side opposite the first side to a desired shape after intended outward growth of the selected body part of the associated user;
  placing the orthotic system on the selected body part of the associated user;
  with the orthotic system on the selected body part of the associated user and with the spacer material disposed between the selected body part and the inner wall of the shell member, allowing the resilient material to cure and harden in situ on the selected body part of the associated user; and,
  after the resilient material cures and hardens in situ on the selected body part of the associated user, removing the spacer material from between the resilient material and the body part of the associated user.

40. The method according to claim 39, further comprising:
  estimating a head volume irregularity of the associated user;
  providing the spacer material in accordance with the estimated head volume irregularity; and,
  manually molding the spacer material to the head volume irregularity of the associated user.

41. The method according to claim 39, further comprising:
  mixing a molding agent;
  injecting the mixed molding agent into a bladder of the resilient material; and,
  permitting gas emitted from the mixed molding agent to escape from within the bladder via a plurality of vent holes provided in the bladder.

42. The method according to claim 39, wherein:
  the providing the orthotic system comprising the resilient material comprises providing a bladder configured to receive a molding agent within the bladder; and
  the allowing the resilient material to cure and harden in situ on the selected body part of the associated user comprises injecting a molding agent into the bladder and allowing the molding agent to cure and harden within the bladder.

* * * * *